(12) United States Patent
Darius et al.

(10) Patent No.: US 7,166,337 B2
(45) Date of Patent: Jan. 23, 2007

(54) LIQUID-CRYSTAL COMPOSITION, METHODS OF ADJUSTING THE RESISTANCE, AND SUBSTITUTED PHENOLS

(75) Inventors: Michael Darius, Darmstadt (DE); Volker Reiffenrath, Rossdorf (DE); Kazuaki Tarumi, Seeheim (DE); Bernhard Rieger, Muenster (DE); Michael Heckmeier, Bensheim (DE); Marcus Reuter, Darmstadt (DE); Peer Kirsch, Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/907,654

(22) Filed: Jul. 19, 2001

(65) Prior Publication Data
US 2002/0084444 A1 Jul. 4, 2002

Related U.S. Application Data

(63) Continuation of application No. 09/658,112, filed on Sep. 8, 2000, now abandoned, which is a continuation of application No. 09/243,803, filed on Feb. 3, 1999, now Pat. No. 6,139,925.

(30) Foreign Application Priority Data

| Feb. 4, 1998 | (DE) | ............................... 198 04 300 |
| Feb. 13, 1998 | (DE) | ............................... 198 05 912 |
| Nov. 11, 1998 | (DE) | ............................... 198 51 805 |

(51) Int. Cl.
| C09K 19/52 | (2006.01) |
| C09K 19/54 | (2006.01) |
| C07C 33/20 | (2006.01) |
| C07C 33/34 | (2006.01) |
| C07C 39/24 | (2006.01) |
| C07C 39/27 | (2006.01) |
| C07C 205/21 | (2006.01) |

(52) U.S. Cl. ............... 428/1.1; 252/299.01; 252/299.5; 568/705; 568/715; 568/716; 568/774; 568/775; 568/807; 568/812; 568/927; 568/928

(58) Field of Classification Search ................ 428/1.1; 252/299.01, 299.5, 299.6; 568/705, 715, 568/716, 774, 775, 807, 812, 927, 928
See application file for complete search history.

(56) References Cited

U.S. PATENT DOCUMENTS

| 1,737,842 A | * | 9/1927 | Hale et al. .................... 568/716 |
| 4,657,707 A | * | 4/1987 | Muller et al. ................ 552/244 |
| 5,053,507 A | | 10/1991 | Moriuchi et al. |
| 5,068,389 A | | 11/1991 | Wachtler et al. |
| 5,217,643 A | | 6/1993 | Yoshida et al. |
| 5,342,544 A | | 8/1994 | Naito et al. |
| 5,723,065 A | | 3/1998 | Inaba et al. |
| 5,858,269 A | | 1/1999 | Shinjo et al. |
| 5,985,170 A | | 11/1999 | Inaba et al. |
| 6,139,925 A | * | 10/2000 | Darius et al. ................ 428/1.1 |

OTHER PUBLICATIONS

CAPLUS 1957: 81284.*

* cited by examiner

Primary Examiner—Shean C Wu
(74) Attorney, Agent, or Firm—Millen, White, Zelano & Branigan, P.C.

(57) ABSTRACT

The present invention relates to liquid-crystal mixtures having specific resistance values, comprising acidic compounds. The present invention furthermore relates to liquid-crystal displays containing these liquid-crystal mixtures. The invention furthermore relates to compounds of the formula I,

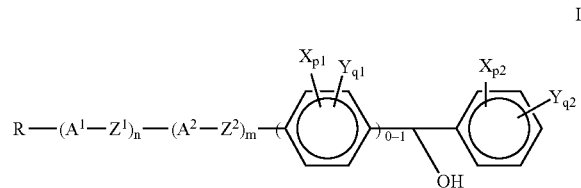

in which the parameters are as defined in the text, to their preparation, and to their use for achieving certain specific resistance values in liquid-crystal mixtures. The application also relates to a method of adjusting the specific resistance of liquid-crystal mixtures using acidic compounds.

17 Claims, No Drawings

LIQUID-CRYSTAL COMPOSITION, METHODS OF ADJUSTING THE RESISTANCE, AND SUBSTITUTED PHENOLS

BACKGROUND OF THE INVENTION

1. Field of the Invention

This invention relates to liquid-crystal mixtures having certain resistance values, and to a method of adjusting the specific resistance of liquid-crystal mixtures to prespecified values, typically in the range from $10^9$ Ω·cm to a few $10^{12}$ Ω·cm. This also applies in particular to liquid-crystal mixtures which comprise or even consist of terminally fluorinated compounds or compounds carrying terminally fluorinated substituents, and in general to high-resistance liquid-crystal mixtures of low polarity.

In particular, the resistance is adjusted using acidic compounds, particularly preferably phenols. The present invention also relates to novel substituted phenols. The present invention furthermore relates to liquid-crystal displays containing liquid-crystal mixtures according to the invention.

2. Description of the Prior Art

Liquid-crystal mixtures having high specific resistance values cause problems in some types of liquid-crystal display.

A major problem of these high-resistance liquid-crystal mixtures is the occurrence of electrostatic charges. This sometimes happens simply when protective films, for example of polarizers, or compensation films are peeled off during production of the displays. However, electrostatic charging can also occur during operation of such displays, for example due to contact and/or friction with plastic parts or cloths. In automobile radio displays, for example, electrostatic charges of this type can even occur due to finger contact with the display. In the simplest case, this electrostatic charge can result in undesired switching on of a switched-off display or part of the display.

Frequently, however, irreversible changes to the display are observed. These are caused, for example, by a change to the alignment layers by the electrostatic charges. This phenomenon is observed in particular in TN and STN displays. In displays of this type, a high specific resistance of the liquid-crystal mixture frequently also results in information which has been displayed for an extended period remaining even after the display has been switched off. Owing to the high specific resistance of the liquid-crystal mixtures, accumulated charge carriers can only be dispersed with difficulty, causing the occurrence of so-called "afterimages" or "ghost images", often also referred to as the "sticking effect" or "image sticking effect". In displays with active matrix addressing (for example TN-AMDs or IPS-AMDs), the active matrix's non-linear switches (for example TFTs), in particular, can be damaged or even destroyed. "Image sticking effects" can also occur in AMDs.

A number of proposals for solving this problem have already been made in the prior art. Besides equipment measures, intended to prevent the occurrence of electrostatic charging in, for example, the production of liquid-crystal displays, a number of suggestions have been described for optimizing the liquid-crystal mixtures.

Most of these suggestions propose the use of various dopants in order to achieve the desired resistance values. However, the solubility of the dopants in the liquid-crystal mixtures is usually problematic here. Furthermore, undesired effects, such as, for example, the lowering of the clearing point and changes in the other physical properties, frequently occur. The reproducibility of the setting of the desired resistance is frequently also not good or the range of achievable resistance values is relatively narrow.

A further essential property of the compounds employed to adjust the conductivity or specific resistance of liquid-crystal mixtures is their vapor pressure. This must not be too high, as must that of the other constituents of the liquid-crystal mixtures, since otherwise a change in the composition can occur, resulting here precisely in an undesired change in the resistance. This is of particular importance in the extremely widespread use of vacuum filling units in display manufacture. The changes which occur seem to be dependent on the duration and magnitude of the pressures which occur.

A typical example of compounds recently used to set certain specific resistance values in liquid-crystal mixtures are crown ethers, used as described in WO 97-03 164. However, even when used in small amounts, these result in very considerable reductions in the resistance.

In addition, owing to the interaction of the crown ethers with various impurities, both in the liquid-crystal mixtures and on the internal display surfaces, i.e. essentially the alignment layers, the results achieved are very highly dependent on the material used, and the reproducibility is frequently inadequate. There was thus a demand for substances for the reproducible adjustment of the specific resistance which are readily soluble in liquid-crystal mixtures and are compatible with many alignment layers.

Compounds of the formulae

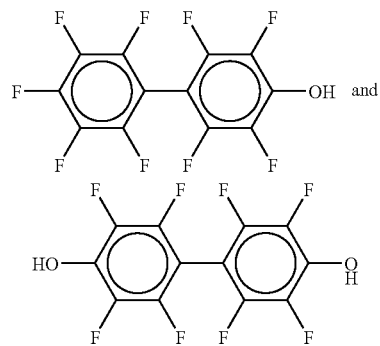

are known, see, for example, Chemical Abstracts CAS-2894-87-3 and CAS-2200-70-6.

JP-A 08-067 577 proposes tri(polyoxyalkylene)amine for reducing the specific resistance of liquid-crystal mixtures.

JP-A 08-337 778 describes liquid-crystal mixtures containing peroxide-destroying compounds for use in STN displays.

DESCRIPTION OF THE PRESENT INVENTION

The present invention had the object of providing liquid-crystal mixtures having prespecified specific resistance values. A further object was thus to select or provide substances which allow the specific resistance of liquid crystals to be adjusted reproducibly.

Surprisingly, this has been achieved by using acidic compounds and in particular acidic phenols, very particularly those of the general formula I

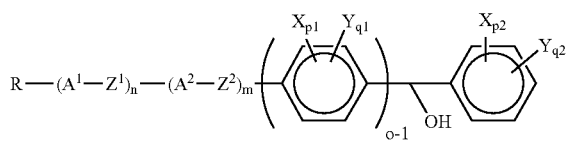

in which
A¹ and A² are each, independently of one another and in the case where A¹ occurs a number of times, these too independently of one another:
a) 1,4-cyclohexylene or trans-1,4-cyclohexenylene, in which, in addition, one or more non-adjacent $CH_2$ groups may be replaced by O and/or S,
b) 1,4-phenylene, in which, in addition, one or two CH groups may be replaced by N,
c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
in which (a) and (b) may be monosubstituted or disubstituted by F atoms,
$Z^1$ and $Z^2$ are each, independently of one another and in the case where $Z^1$ occurs a number of times, these too independently of one another:
—CO—O—, —O—CO—, —CO—$CH_2$—, —$CH_2$—CO—, —$CH_2$O—, —O$CH_2$—, —$CH_2CH_2$—, —CH=CH—, —C≡C— or a single bond, or one of the groups $Z^1$ and $Z^2$ is
—$(CH_2)_4$—, —$(CH_2)_3$CO—, —$(CH_2)_2$—O—CO—, —$(CH_2)_2$—(CO—O)—, CH=CH—$CH_2CH_2$—, —$CH_2$—$CH_2$—CH=CH— or —$CH_2$—CH=CH—$CH_2$—,
R is H, alkyl or alkenyl having 1 or 2 to 15 carbon atoms respectively, which are unsubstituted, monosubstituted by CN or $CF_3$ or monosubstituted or polysubstituted by halogen, in particular F or Cl, where, in addition, one or more $CH_2$ groups in these radicals may be replaced, independently of one another, by —O—, —S—,

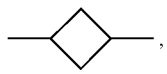

—CO—, —CO—O—, —O—CO— or —O—CO—O— in such a way that no two O atoms are bonded directly to one another,
or
CN, F, Cl or COOR', if appropriate also OH,
R' is H or R, where CN, F, OH and COOR' are excluded,
n is 0, 1 or 2,
m is 0 or 1,
o is 1, 2 or 3,
n+m+o is 2, 3 or 4,
X and Y are each, independently of one another and in the case where X and/or Y occur a number of times, these too independently of one another, are F, Cl, COOR', $NO_2$ or CN, where X is preferably F and Y is preferably CN,
$p_1$, $p_2$,
$q_1$ and $q_2$ are each 0, 1, 2, 3 or 4,
one of $q_1$ and $q_2$, preferably $q_2$, is preferably 1
where o is 1 and $q_2$ is 0
p2 is 3 or 4
where o is 1 and $q_2$ is 1, 2 or 3
$p_2+q_2$ is 1, 2, 3 or 4
preferably $q_2$ is 1 and $p_2$ is 1 or 2
where o is 2 or 3
$p_1+p_2+$
$q_1+q_2$ is 1, 2, 3, 4, 5, 6, 7, or 8,
where $q_1+q_2$ is 1 or 2
$p_1+p_2$ is 1, 2, 3 or 4
preferably
$q_1+q_2$ is 1 and $p_1+p_2$ is 1 or 2
where $q_1+q_2$ is 0
$p_1+p_2$ is 3, 4, 5, 6, 7 or 8
preferably 6, 7 or 8
Preference is given to compounds of the formula Ia

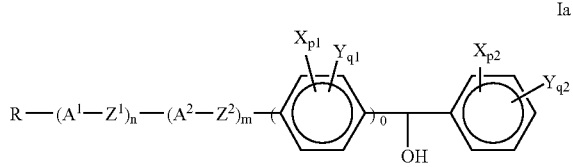

in which
A¹ and A² are each, independently of one another and in the case where A¹ occurs a number of times, these too independently of one another:
a) 1,4-cyclohexylene or trans-1,4-cyclohexenylene, in which, in addition, one or more non-adjacent $CH_2$ groups may be replaced by O and/or S,
b) 1,4-phenylene, in which, in addition, one or two CH groups may be replaced by N,
c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
in which (a) and (b) may be monosubstituted or disubstituted by F atoms,
$Z^1$ and $Z^2$ are each, independently of one another and in the case where $Z^1$ occurs a number of times, these too independently of one another:
—CO—O—, —O—CO—, —CO—$CH_2$—, —$CH_2$—CO—, —$CH_2$O—, —O$CH_2$—, —$CH_2CH_2$—, —CH=CH—, —C≡C— or a single bond, or one of the groups $Z^1$ and $Z^2$ is
—$(CH_2)_4$—, —$(CH_2)_3$CO—, —$(CH_2)_2$—O—CO—, —$(CH_2)_2$—(CO—O)—, CH=CH—$CH_2CH_2$—, —$CH_2$—$CH_2$— CH=CH— or —$CH_2$—CH=CH—$CH_2$—,
R is H, alkyl or alkenyl having 1 or 2 to 15 carbon atoms respectively, which are unsubstituted, monosubstituted by CN or $CF_3$ or monosubstituted or polysubstituted by halogen, in particular F or Cl, where, in addition, one or more $CH_2$ groups in these radicals may be replaced, independently of one another, by —O—, —S—,

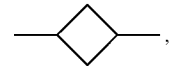

—CO—, —CO—C—, —O—CO— or —O—CO—O— in such a way that no two O atoms are bonded directly to one another,
or
CN, F, Cl or COOR', if appropriate also OH, R' is H or R, where CN, F and COOR' are excluded,
n is 0, 1 or 2,
m is 0 or 1,
o is 1, 2 or 3,
n+m+o is 2, 3 or 4,
X and Y are each, independently of one another and in the case where X and/or Y occur a number of times, these too independently of one another, are F, Cl, COOR', $NO_2$ or CN, where X is preferably F and Y is preferably CN,
one of $q_1$ and $q_2$, preferably $q_2$, is preferably 1
   where o is 1 and $q_2$ is 0
      p2 is 3 or 4
   where o is 1 and $q_2$ is 1, 2 or 3
      $p_2+q_2$ is 1, 2, 3 or 4
      preferably $q_2$ is 1 and $p_2$ is 1 or 2
   where o is 2 or 3
      $p_1+p_2+$
      $q_1+q_2$ is 1, 2, 3, 4, 5, 6, 7, or 8,
   where $q_1+q_2$ is 1 or 2
      $p_1+p_2$ is 1, 2, 3 or 4
      preferably
      $q_1+q_2$ is 1 and $p_1+p_2$ is 1 or 2
   where
      $q_1+q_2$ is 0
      $p_1+p_2$ is 3, 4, 5, 6, 7 or 8
      preferably 6, 7 or 8

In formula I and Ia, the hydroxy-group may be located at the terminal phenyl group and/or other phenyl groups, where present. Compounds with hydroxy groups only on the terminal phenyl group are of subformulae I' and Ia':

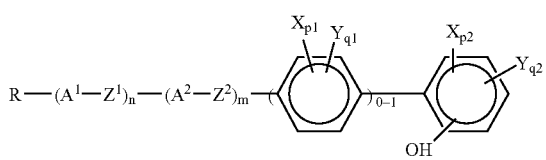

I'

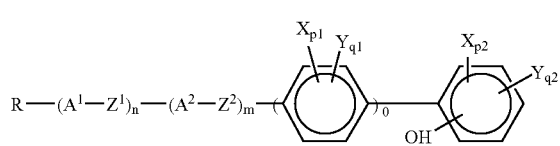

I'a

Preference is furthermore given to compounds of the formula Ib

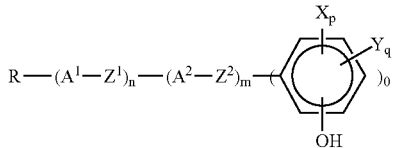

Ib in which
$A^1$ and $A^2$ are each, independently of one another and in the case where $A^1$ occurs a number of times, these too independently of one another:
  a) 1,4-cyclohexylene or trans-1,4-cyclohexenylene, in which, in addition, one or more non-adjacent $CH_2$ groups may be replaced by O and/or S,
  b) 1,4-phenylene, in which, in addition, one or two CH groups may be replaced by N,
  c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
in which (a) and (b) may be monosubstituted or disubstituted by F atoms,
$Z^1$ and $Z^2$ are each, independently of one another and in the case where $Z^1$ occurs a number of times, these too independently of one another:
  —CO—O—, —O—CO—, —CO—$CH_2$—, —$CH_2$—CO—, —$CH_2$O—, —$OCH_2$—, —$CH_2CH_2$—, —CH=CH—, —C≡C— or a single bond, or one of the groups $Z^1$ and $Z^2$ is
  —$(CH_2)_4$—, —$(CH_2)_3$CO—, —$(CH_2)_2$—O—CO—, —$(CH_2)_2$—(CO—O)—, CH=CH—$CH_2CH_2$—, —$CH_2$—$CH_2$—CH=CH— or —$CH_2$—CH=CH—$CH_2$—,
R is H, alkyl or alkenyl having 1 or 2 to 15 carbon atoms respectively, which are unsubstituted, monosubstituted by CN or $CF_3$ or monosubstituted or polysubstituted by halogen, in particular F or Cl, where, in addition, one or more $CH_2$ groups in these radicals may be replaced, independently of one another, by —O—, —S—,

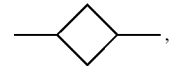

—CO—, —CO—O—, —O—CO— or —O—CO—O— in such a way that no two O atoms are bonded directly to one another,
or
CN, F, Cl or COOR', if appropriate also OH,
R' is H or R, where CN, F and COOR' are excluded,
n is 0, 1 or 2,
m is 0 or 1,
o is 1, 2 or 3,
n+m+o is 2, 3 or 4,
X and Y are each, independently of one another and in the case where X and/or Y occur a number of times, these too independently of one another, are F, Cl, COOR', $NO_2$ or CN, where X is preferably F and Y is preferably CN,
p and q are 0, 1, 2 or 3,
p+q is 1, 2, 3, 4, 5, 6, 7 or 8,
q is preferably 0 or 1,
and, in the case where q=0,
p is 3, 4, 5, 6, 7 or 8,
in the case where q=1,
p is 1, 2, 3, 4, 5, 6, or 7,
and X is preferably F and Y is preferably CN.

In the formula Ia,

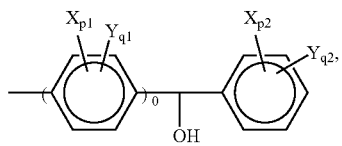

is preferably, where o=1,

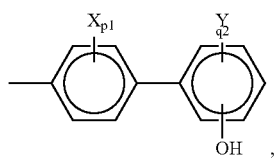

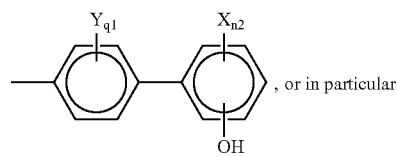, or in particular

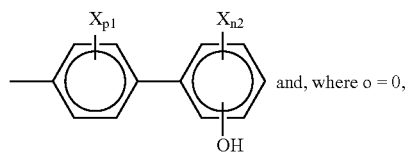 and, where o = 0,

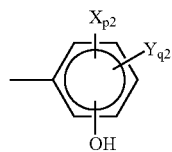

in which $X_{p1}$, $X_{p2}$, $Y_{q1}$ and $Y_{q2}$ are as defined above under the formula Ia.

In the formula Ib,

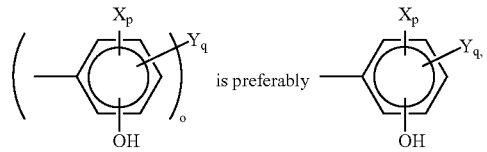 is preferably

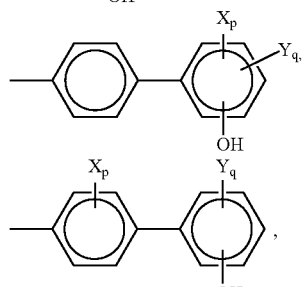

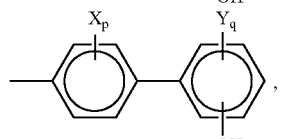

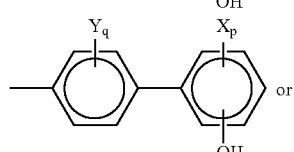 or

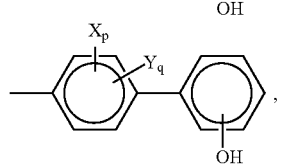

in which
X is F, Cl or COOR', preferably F,
Y is CN or NO$_2$, preferably CN
p and q are each 0, 1, 2 or 3, and
p+q is 2 or 3, and, in the case where R=CN, F, Cl, OH or COOR', is alternatively 1.

In the formula Ib,

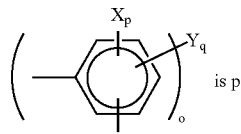 is particularly preferably

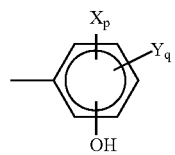

in which $X_p$ and $Y_q$ are as defined under formula Ib.

X is preferably F. Y is preferably CN.

Particular preference is given to compounds of the subformulae Ia-1 to Ia-6

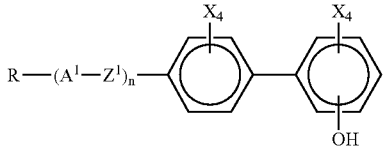 Ia-1

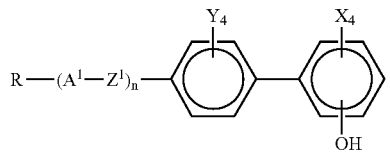 Ia-2

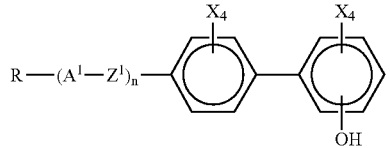 Ia-3

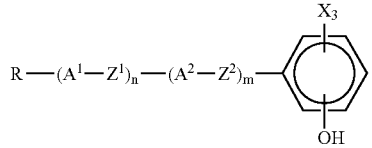 Ia-4

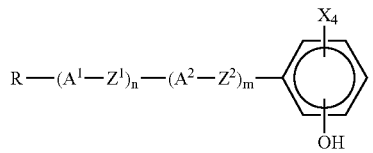 Ia-5

-continued

Ia-6

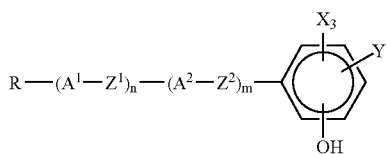

in which

R, $A^1$, $A^2$, $Z^1$, $Z^2$, n, m, X and Y are as defined above under the formula Ia. Y is preferably CN, X is preferably F, n is preferably 0, and R is preferably CN, F or OH.

Particular preference is given to compounds of the subformulae Ib-1 to Ib-5.

Ib-1

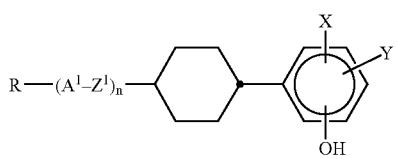

Ib-2

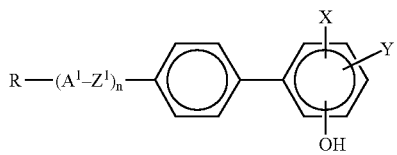

Ib-3

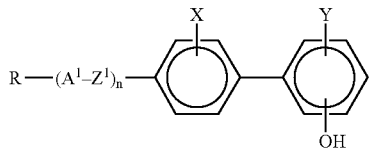

Ib-4

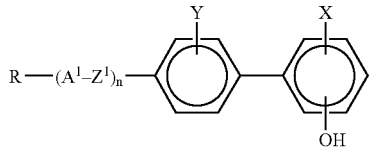

Ib-5

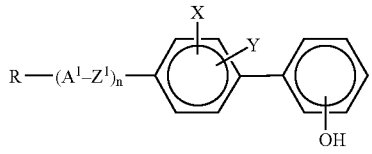

in which R, $A^1$, $Z^1$, n, X and Y are as defined above under the formula Ib. Y is preferably CN, and X is preferably F.

Particular preference is given to compounds of the subformulae Ia-3a, Ia-4a, Ia-5a and Ia-6a:

Ia-3a

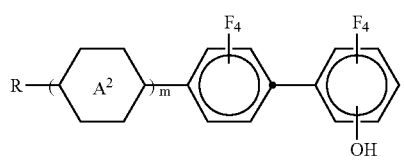

-continued

Ia-4a

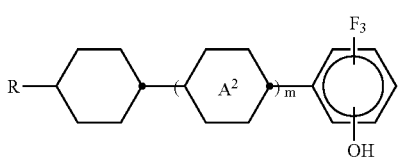

Ia-5a

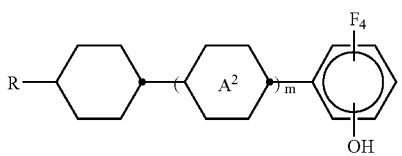

Ia-6a

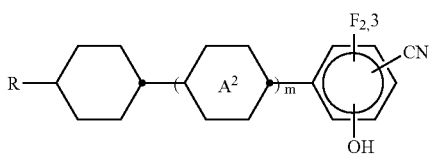

in which R, $A^2$ and m are as defined above under the formula I.

In the subformulae Ia-3a, Ia-4a, Ia-5a and Ia-6a,

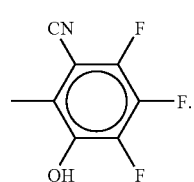 is preferably

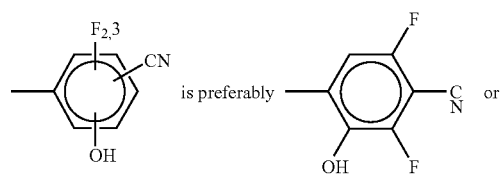

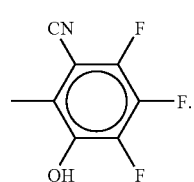

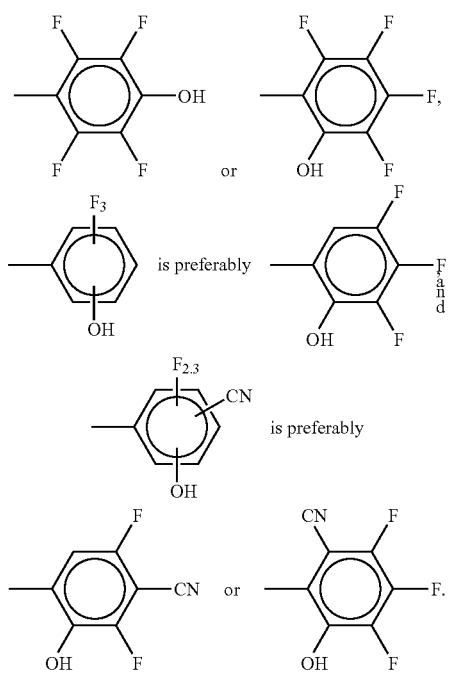

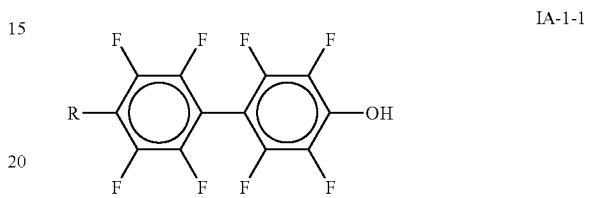

Very particular preference is given to compounds of the formula Ia-1-1

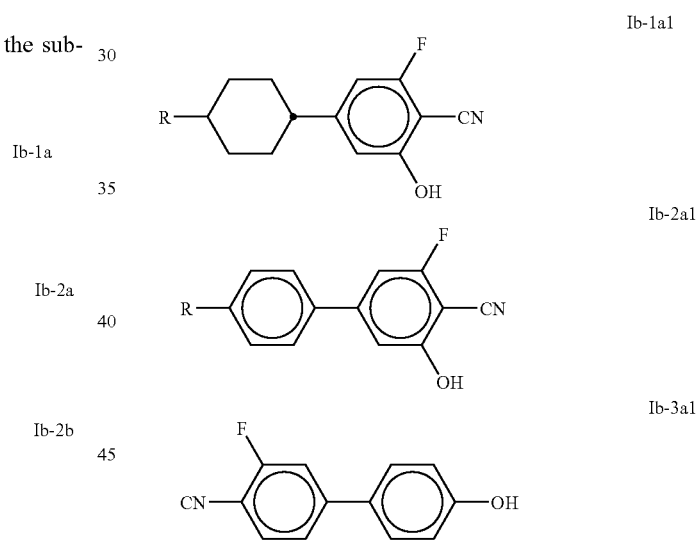

in which R is CN, F, Cl or OH, preferably F.

Very particular preference is furthermore given to compounds of the formulae Ib-1a1, Ib-2a1 and Ib-3a1:

Particular preference is given to compounds of the subformulae Ib-1a, Ib-2a and Ib-2b:

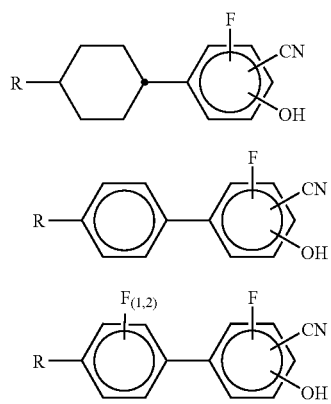

in which R is as defined above under the formula I.

In the subformulae Ib-1a, 1b-2a and Ib-2b,

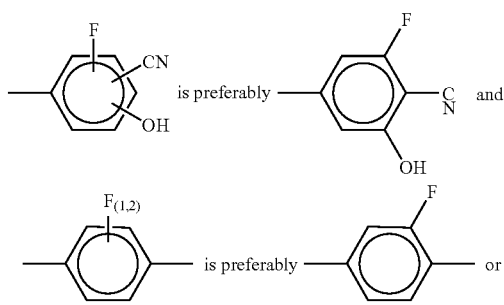

in which R is as defined above under the formula I. In the case of compounds of the formula Ib-1a1, R is particularly preferably alkyl or alkenyl having 1 to 7 carbon atoms, very particularly preferably ethyl, propyl, butyl or pentyl. In the case of compounds of the formula Ib-2a1, R is particularly preferably alkyl or alkoxy having 1 to 7 carbon atoms, very particularly preferably methoxy, ethoxy, propoxy or butoxy.

Besides liquid-crystal mixtures comprising the above-mentioned phenol compounds, the present application also relates to these compounds themselves, as long as they were still unknown. These liquid-crystal mixtures are particularly suitable for use in liquid-crystal displays, especially for STN and IPS displays.

Liquid-crystal mixtures for STN displays and especially the liquid-crystal display mixture concepts which are favourable for such displays are described in EP 0 394 417, and those of AMD displays are described in EP 0 394 419.

Liquid-crystal mixtures for TN displays in accordance with the present application preferably comprise terminally cyano-substituted compounds as dielectrically positive compounds. They very particularly preferably comprise compounds of the formula II

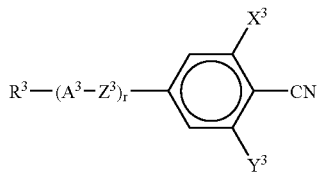

II in which

A³, in the case where A³ occurs a number of times, these independently of one another, is
a) 1,4-cyclohexylene or trans-1,4-cyclohexenylene, in which, in addition, one or more non-adjacent CH₂ groups may be replaced by O and/or S,
b) 1,4-phenylene in which, in addition, one or two CH groups may be replaced by N,
c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl, in which (a) and (b) may be monosubstituted or disubstituted by F atoms, Z³ in the case where Z³ occurs a number of times, these independently of one another, is
—CO—O—, —O—CO—, —CO—CH₂—, —CH₂—CO—, —CH₂O—, —OCH₂—, —CH₂CH₂—, —CH═CH—, —C≡C— or a single bond, R³ is H, alkyl or alkenyl having 1 or 2 to 15 carbon atoms respectively, which are unsubstituted, monosubstituted by CN or CF₃ or monosubstituted or polysubstituted by halogen, in particular F or Cl, where, in addition, one or more CH₂ groups in these radicals may be replaced, independently of one another, by —O—, —S—,

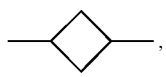

—CO—, —CO—O—, —O—CO— or —O—CO—O—
in such a way that no two O atoms are directly bonded to one another, r is 1 or 2,
X³ is H or F, and
Y³ is H or F.

The mixtures preferably comprise compounds of the formula II-1 and, if desired, II-2

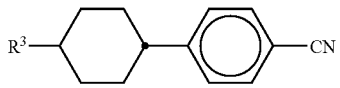

II-1

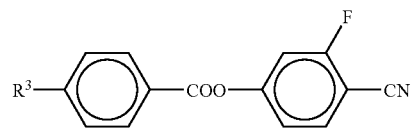

II-2 in which R³ is as defined above under the formula II and is preferably n-alkyl or 1-E-alkenyl.

Preference is given to liquid-crystal mixtures comprising dielectrically positive compounds of the formula II where r=1, A³=1,4-cyclohexylene, X³=H, Z³ is a single bond, Y³=H, and R=alkyl or alkenyl having 1 or 2 to 7 carbon atoms, respectively. In particular, the liquid-crystal mixtures are based on these compounds, at least regarding their dielectrically positive constituents. This applies in particular to the mixtures for TN displays and also for STN displays. Compounds of the formula II where r=1, A³=1,4-phenylene, Z³=—CO—O—, X³=H, Y³=F and R=alkyl or alkenyl having 1 or 2 to 7 carbon atoms respectively are also present in preferred liquid-crystal mixtures. However, the concentration of the compounds of the formula II-2 is generally significantly lower than that of the compounds of the formula II-1. The threshold voltage of the preferred liquid-crystal mixtures is, preferably in TN cells, preferably in the range from 1.5 V to 4.0 V, very particularly preferably from 1.8 to 3.5 V, especially preferably from 2.0 to 3.0 V.

With regard to the liquid-crystal mixtures and liquid-crystal mixture concepts for STN and AMD displays, EP 394417 and EP 394419 mentioned above are incorporated into the present application by way of reference.

For TN and STN displays, particularly preferred liquid-crystal mixtures in accordance with the present application are those comprising terminally cyano-substituted compounds, such as, for example, benzonitriles and benzonitriles which are monosubstituted or disubstituted by fluorine in the ortho position to the cyano group.

The liquid-crystal mixtures for STN displays in accordance with the present application may also comprise terminally fluorinated compounds and/or compounds carrying terminally fluorine-containing substituents.

Liquid-crystal mixtures for STN displays according to the present application very particularly preferably comprise compounds containing alkenyl side chains. These compounds can be either dielectrically positive and contain an alkenyl side chain or dielectrically neutral. In the latter case, the compounds can contain one or two alkenyl side chains.

In liquid-crystal mixtures for AMD displays, preference is given in the present application to terminally fluorinated compounds and/or compounds carrying terminally fluorine-containing substituents. These mixtures preferably comprise at most 10%, particularly preferably at most 5%, very particularly preferably at most 1%, of cyano-substituted compounds. In particular, such mixtures comprise no cyano-substituted compounds apart from, if desired, those of the formula I and its subformulae.

The compounds according to the invention or the compounds used according to the invention are particularly preferably used in mixtures for IPS displays. For such IPS displays, preference is given in the present application to liquid-crystal mixtures comprising terminally fluorinated compounds, like the mixtures for AMD displays. However, the mixtures for IPS displays additionally comprise terminally cyano-substituted compounds. The concentration of these terminally cyano-substituted compounds can vary within broad limits.

In particular, it is not restricted to a low upper limit as in the case of the mixtures for AMD displays. Typically, from 1 to 50% of cyano-substituted compounds can be employed. Preference is given to mixtures comprising from 5 to 35%, particularly preferably from 7 to 25%, of cyano-substituted compounds.

Liquid-crystal mixtures for IPS displays and mixture concepts for these liquid-crystal displays are described in GB 23 10 669, EP 0 807 153, DE 19528104, DE 19528107, EP 0 768 359, DE 19 611 096 and DE 19 625 100. These seven patent applications are incorporated herein by way of reference regarding liquid-crystal mixtures for IPS displays and regarding their mixture concepts.

The structure of the TN, STN, AMD and IPS displays is known or follows known rules. The terms TN, STN, AMD and IPS here are broadly drawn and also cover typical modifications of displays of these types.

The structure of STN displays is described in EP 0 098 070, EP 0 131 216 and EP 0 260 450 and that of IPS displays is described, inter alia, in U.S. Pat. No. 5,576,867 and EP 0 588 568. Regarding the construction of STN and IPS displays, the abovementioned five patent applications are incorporated herein by way of reference.

Synthesis of the Compounds

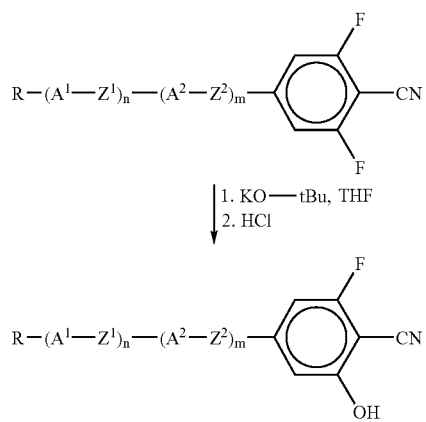

R, $A^1$, $Z^1$, $A^2$, $Z^2$, n and m are as defined above under the formula I.

The compounds according to the invention are added to the liquid-crystal mixtures in concentrations of from 1 ppm to typically 50,000 ppm, preferably 10 ppm to 10,000 ppm, particularly preferably 50 ppm to 5000 ppm (based on proportions by weight).

The physical properties are determined, unless described otherwise, as described in "Physical Properties of Liquid Crystals", Merck KGaA, Ed. W. Becker, Nov. 1997.

The specific resistances (abbreviated to SR) of the liquid-crystal mixtures per se are determined as described in G. Weber et al. "Liquid crystals for active matrix displays", Liquid crystals, 1989, Vol. 5, No. 5, pages 1381–1388, using 1 ml in a stainless-steel measurement cell.

The specific resistances of the liquid-crystal mixtures are furthermore determined in glass test cells (SRZ). These test cells consist, like liquid-crystal display cells, of two glass plates bonded parallel to one another at a distance from one another. The cells are produced in the test cell manufacturing facility at Merck KGaA. They consist of alkali-free glass with indium tin oxide (ITO) electrodes with no alignment layer. The layer thickness is 20 µm. The cells have two fill openings on opposite sides. The electrodes are circular, each having an area of 1 $cm^2$. For screening against electromagnetic radiation, the cells are provided with a ring-shaped protective electrode.

The specific resistance of the liquid-crystal mixtures in test cells (SRZ) is, like the specific resistance as such (SR), measured using a sensitive electrometer (Keithley 6517 High-resistance system). The Keithley 617 is used when measuring the specific resistance as such (SR). The filling of the dried cells and the measurement of the resistance all take place in a system of glove boxes connected by air locks. A stream of dry nitrogen passes continuously through these glove boxes. The relative atmospheric humidity inside the boxes containing the cells must be lower than 10%, in particular during filling and measurement of the cells.

The resistance is measured in an aluminium housing in which the test cells are held at 20° C. by means of two brass blocks with water as heating medium.

For shielding against stray electromagnetic fields, the guard ring of the measurement cells is earthed together with the aluminium housing.

The earthing of the guard ring is implemented separately for each of the measurement lines and together with the earthing of the aluminium housing in such a way that earth loops do not form.

The capacitance of the cells in the discharged state is determined separately before filling. It is typically $\epsilon_{empty}$=45 pF.

In order to determine the resistance, the current is measured at a constant direct voltage of 20 V. To this end, the test cell is addressed as follows. After a waiting time of 20 s, four 20 V pulses of alternating polarity are applied. All four pulses are 20 s in width and separated from one another by a 0 V interval of 20 s. The last of the four pulses is followed by a 0 V interval of 180 s, and then 20 V with the polarity of the first pulse is again applied for 180 s. At the end of this final pulse, ten measurement readings are taken within 5 s; these give the average resistance.

The heating is carried out in another of the three glove boxes. After the heating, typically at 120° C. for 1 hour, the cell is allowed to cool and then transferred back into the glove box together with the temperature-maintained cell holder.

The resultant specific resistance (SR) values of the finished liquid-crystal mixtures are from $10^9$ Ωcm to $10^{13}$ Ωcm, depending on the area of application and the specification. Liquid-crystal mixtures for TN and STN displays preferably have specific resistance values of from $10^{10}$ Ωcm to $10^{12}$ Ωcm, especially from $5·10^{10}$ Ωcm to $2·10^{11}$ Ωcm, and liquid-crystal mixtures for IPS displays preferably have specific resistance values of from $5·10^{11}$ Ωcm to $8·10^{12}$ Ωcm, preferably from $10^{12}$ Ωcm to $3·10^{12}$ Ωcm.

Concentrations of dopant in the range from 10 to 1000 ppm are particularly preferably employed and specific resistances in cells (SRZ) of from $5·10^{11}$ Ωcm to $1·10^{13}$ Ωcm are obtained. Relatively small concentrations of dopant are preferred.

The physical properties given above and below in this application apply to and are given for a temperature of 20° C., unless explicitly stated otherwise.

The "Voltage Holding Ratio" (VHR or HR) is measured as described in "Physical Properties of Liquid Crystals", VIII, Voltage Holding Ratio, Merck KGaA, Ed. W. Becker, Nov. 1997. Test cells having a layer thickness of about 5 μm and an electrode area of 1 cm² were used. The voltage holding ratio was determined using a commercially available instrument from Antonic-Melchers, Germany. The measurement voltage was 1 V.

The electrooptical properties, in particular the threshold values and the steepness values, were determined in test cells produced by Merck KGaA. The threshold voltage $V_{th}$ or $V_{10}$ was determined for a 10% change in the relative contrast, i.e. between a non-addressed cell and a cell addressed to full saturation. The steepness was determined as $V_{90}/V_{10}$.

Cells having a twist angle of 90° were used. The cells were operated in normally white mode. The liquid-crystal mixtures were not doped with chiral dopants. The layer thickness of the cells was selected so that the optical retardation was 0.50 μm.

The measuring instruments used were a commercially available instrument from Otsuka, Japan, and a matched measuring instrument from Merck KGaA.

The present application also relates to a method of achieving and adjusting a certain specific resistance in liquid-crystal mixtures by means of acidic mesogenic compounds, preferably by means of appropriately substituted phenols.

The present application relates to a method of adjusting the resistance of liquid-crystal mixtures to a desired value by using acidic, mesogenic or liquid crystal-like compounds. Particular preference is given to acidic compounds having a sufficiently high $pK_a$ value. The minimum values for $pK_a$ depend on the resistance and the polarity (in particular the dielectric anisotropy) of the liquid-crystal mixture. In the case of liquid-crystal mixtures having low resistance values, for example from $10^{10}$ to $10^{11}$ Ωcm, it is necessary to use acidic compounds having larger $pK_a$ values than in the case of the liquid-crystal mixtures having greater resistance values.

The $pK_a$ value of the compound(s) employed (preferably phenol compounds) should be at least as large as that of the compound CCU-3-CN.OH—F from Example 2c (Substance Example 5) (cf. Example 10). The $pK_a$ value of the compound(s) employed is preferably greater than that of CCU-3-CN—OH—F.

The compounds preferably to be employed carry more than 3 fluorine substituents on the OH-substituted ring or, in the case of biphenyl compounds, more than 2 fluorine substituents on each ring.

The compounds particularly preferably carry 7, 8 or 9 fluorine substituents so long as they contain an OH-substituted biphenyl system. The compounds particularly preferably contain one CN and at least one F substitution on the OH-substituted benzene ring. The CN group is preferably in the ortho- or para-position to the OH, particularly preferably in the ortho-position.

It is furthermore necessary to use compounds whose vapour pressure is wherever possible not excessively high. Preference is given to compounds whose vapour pressure is not higher than that of the liquid-crystal compounds usually employed, for example

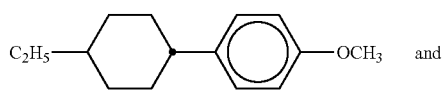

and

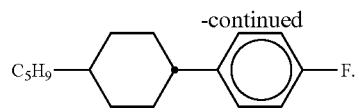

Particular preference is given to compounds whose vapour pressure is not higher than that of

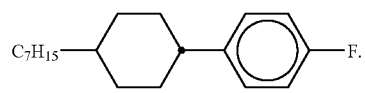

Particular preference is given to acidic phenols, especially compounds of the formula I and its subformulae of the present application.

The construction of the liquid-crystal display elements according to the invention from polarizers, electrode baseplates and electrodes having a surface treatment such that the preferential alignment (director) of the liquid-crystal molecules adjacent thereto is usually twisted from one electrode to another by a value of about 90° (in particular of about 80° to 110°) or from 160° to 720°, corresponds to the usual design for display elements of this type. The term usual design is broadly drawn here and also covers all derivatives and modifications of the TN and STN cell, in particular also matrix display elements and display elements containing additional magnets. The surface tilt angles at the two outer plates can be identical or different. Identical tilt angles are preferred. Preferred TN displays have tilt angles between the long axis of the molecules at the surface of the outer plates and the outer plates of from 0° to 7°, preferably from 0.01° to 5°, in particular from 0.1 to 2°. In STN displays, the tilt angle is from 1° to 30°, preferably from 1° to 12°, in particular from 3° to 8°.

The twist angle of the TN mixture in the cell has a value of from 22.5° to 170°, preferably from 45° to 130°, in particular from 80° to 115°. In a display, the twist angle of the STN mixture from alignment layer to alignment layer has a value of from 100° to 600°, preferably from 170° to 270°, in particular from 180° to 250°.

IPS displays of the present application preferably have an untwisted starting state and are twisted about an axis perpendicular to the substrates by the component of the electric field parallel to the substrates. The tilt angle is preferably in the range from 0° or just above 0° (for example 0.1°) to 15°, particularly preferably from 0.2 to 6°.

The liquid-crystal mixtures which can be used in accordance with the invention are prepared in a manner conventional per se. In general, the desired amount of the components used in lesser amount are dissolved in the components making up the principal constituent, expediently at elevated temperature. It is also possible to mix solutions of the components in an organic solvent, for example in acetone, chloroform or methanol, and, after mixing, to remove the solvent again, for example by distillation.

The liquid-crystal mixtures can also contain further additives known to the person skilled in the art and described in the literature. For example, 0–15% of pleochroic dyes can be added.

The examples below are intended to illustrate the invention without representing a limitation.

The following abbreviations are used:
T(S,N) smectic-nematic phase transition temperature,
T(N,I) nematic-isotropic phase transition temperature,
cl.p. clearing point
$t_{on}$ time from switching on until 90% of the maximum contrast is reached
$t_{off}$ time from switching off until 10% of the maximum contrast is reached
$V_{90}/V_{10}$ steepness $$\frac{t_{on} + t_{off}}{2}$$

Δε dielectric anisotropy
Δn optical anisotropy
SR specific resistance in bulk
SRZ specific resistance in test cells Above and below, all temperatures are given in ° C., the percentages are percent by weight, and the values for the physical properties relate to 20° C., unless otherwise specified.

In the present application and in the examples below, the structures of the liquid-crystal compounds are indicated by acronyms, the transformation into chemical formulae taking place in accordance with Tables A and B below. All radicals $C_nH_{2n+1}$ and $C_mH_{2m+1}$ are straight-chain alkyl radicals having n or m carbon atoms respectively. The alkenyl radicals have the trans-configuration. The coding in Table B is self-evident. In Table A, only the acronym for the parent structure is given. In individual cases, the acronym for the parent structure is followed, separated by a hyphen, by a code for the substituents $R^1$, $R^2$, $L^1$, $L^2$ and $L^3$.

The TN, STN and IPS displays preferably contain liquid-crystal mixtures composed of one or more compounds from Tables A and B.

TABLE A ($L^1$, $L^2$, $L^3$: H or F)

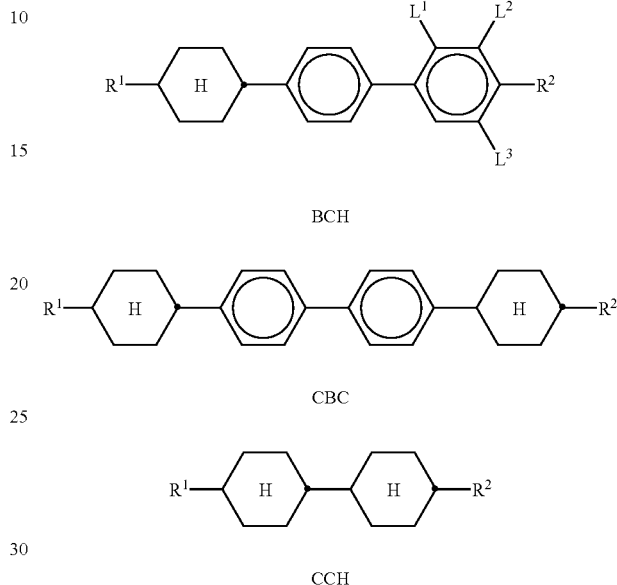

BCH

CBC

CCH

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | H | F |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | H | F |
| nmF | $C_nH_{2n+1}$ | $C_mH_{2m+1}$ | F | H | H |
| $nCF_3$ | $C_nH_{2n+1}$ | $CF_3$ | H | H | H |
| $nOCF_3$ | $C_nH_{2n+1}$ | $OCF_3$ | H | H | H |
| $nOCF_2$ | $C_nH_{2n+1}$ | $OCHF_2$ | H | H | H |
| nS | $C_nH_{2n+1}$ | NCS | H | H | H |
| rVsN | $C_nH_{2n+1}$—CH=CH—$C_sH_{2s}$— | CN | H | H | H |
| rEsN | $C_nH_{2n+1}$—O—$C_2H_{2s}$— | CN | H | H | H |
| nNF | $C_nH_{2n+1}$ | CN | H | F | H |
| nAm | $C_nH_{2n+1}$ | $COOC_mH_{2m+1}$ | H | H | H |
| nF.Cl | $C_nH_{2n+1}$ | Cl | H | H | F |
| n-Vm | $C_nH_{2n+1}$ | —CH=CH—$C_mH_{2m+1}$ | H | H | H |
| nV-Vm | $C_nH_{2n+1}$—CH=CH— | —CH=CH—$C_mH_{2m+1}$ | H | H | H |
| nV-m | $C_nH_{2n+1}$—CH=CH— | —$C_mH_{2m+1}$ | H | H | H |
| nV-N | $C_nH_{2n+1}$—CH=CH— | —CN | H | H | H |
| nV-F | $C_nH_{2n+1}$—CH=CH— | F | H | H | H |
| nV-F.F | $C_nH_{2n+1}$—CH=CH— | F | H | H | F |
| n-2Vm | $C_nH_{2n+1}$ | $C_mH_{2m+1}$—CH=CH—$CH_2CH_2$— | H | H | H |

TABLE A-continued
(L¹, L², L³: H or F)
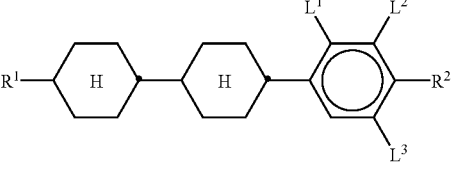
CCP
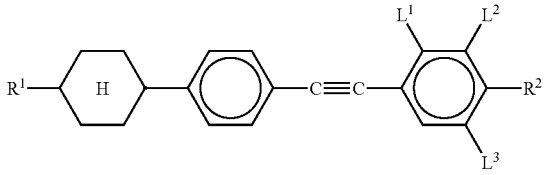
CPTP
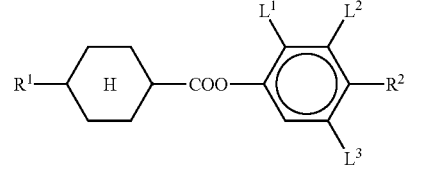
D
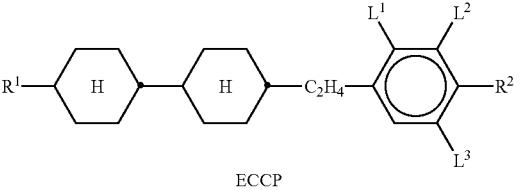
ECCP
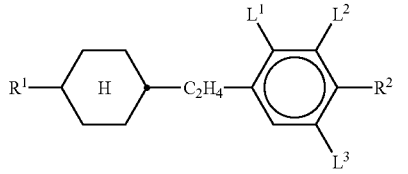
EPCH
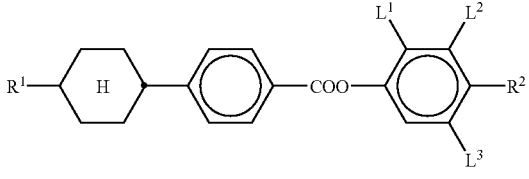
HP
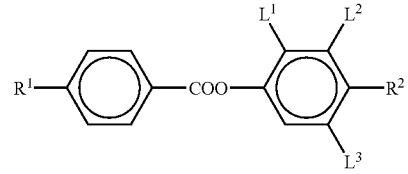
ME
TABLE A-continued
(L¹, L², L³: H or F)
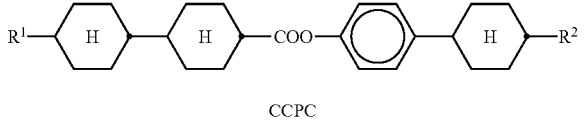
CCPC
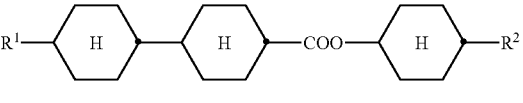
CH
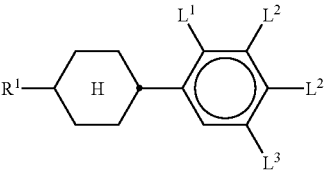
PCH
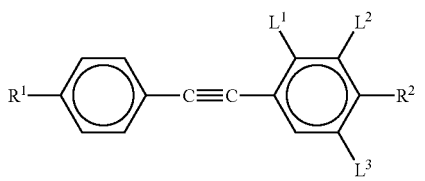
PTP
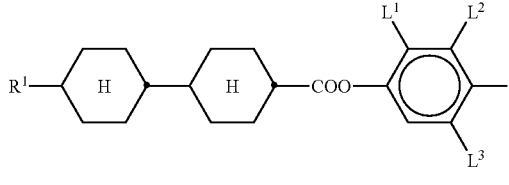
CP
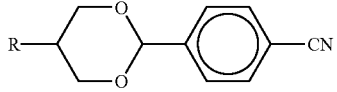
PDX
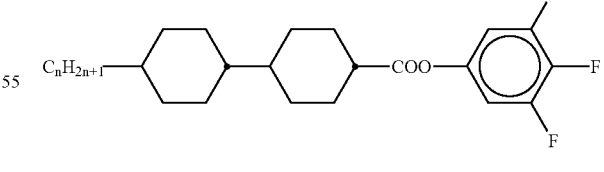
CCZU-n-F
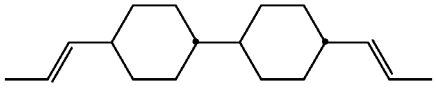
CC-1V-V1

TABLE B

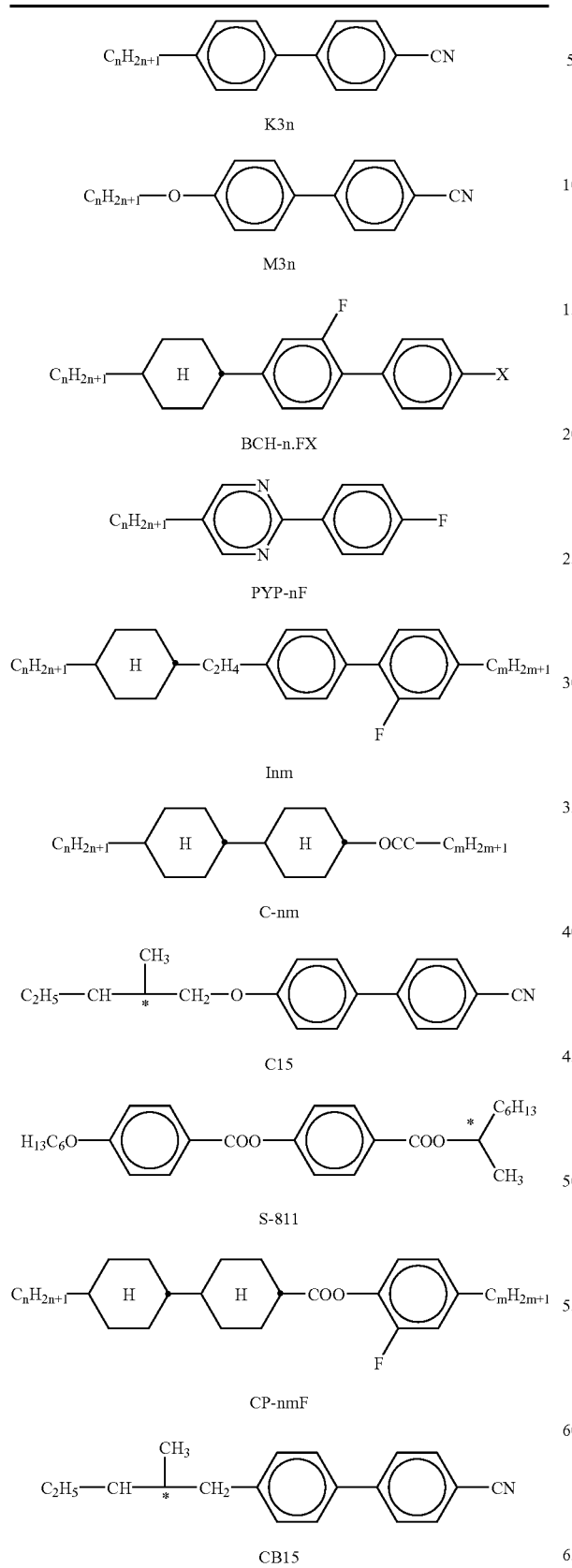

TABLE B-continued

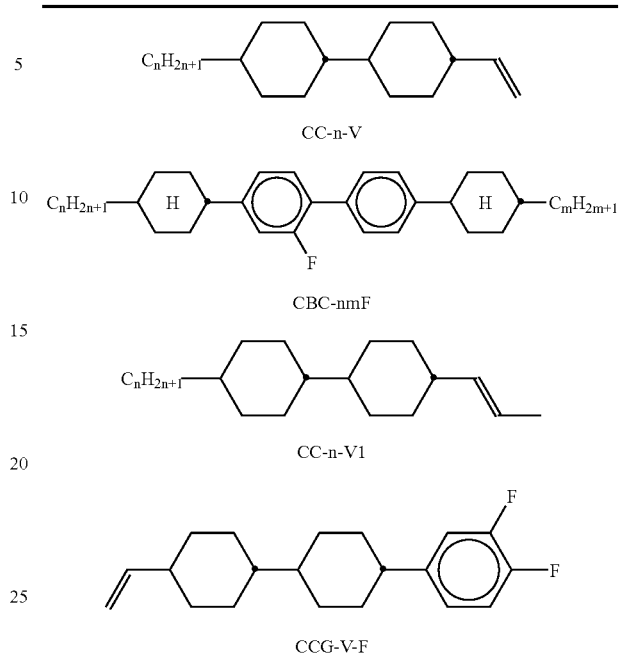

The examples below are intended to illustrate the invention without representing a limitation. Above and below, percentages are percent by weight. All temperatures are given in degrees Celsius. m.p. denotes melting point, cl.p.=clearing point. Furthermore, C=crystalline state, N=nematic phase, S=smectic phase and I=isotropic phase. The data between these symbols are the transition temperatures. Δn denotes optical anistropy (589 nm, 20° C.). Δε denotes the dielectric anisotropy (1 kHz, 20° C.).

EXAMPLES

Example 1

Substance Example

Compound 1

4.1 g of 2,6-difluoro-4-(4-n-propyl-trans-cyclo-hexyl)benzonitrile

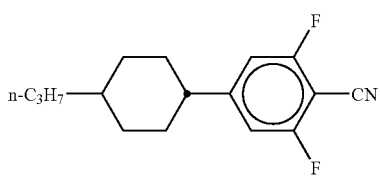

were dissolved in 150 ml of THF, and the solution was introduced into a 250 ml four-neck flask. 1.75 g of potassium tert-butoxide were dissolved in 30 ml of THF, and the solution was slowly added dropwise with stirring at such a rate that the temperature did not exceed 30° C. The reddish reaction mixture was stirred for 12 hours, then hydrolysed using about 40 ml of conc. HCl, whereupon it turned a yellow colour. During the hydrolysis, it was ensured that the temperature did not exceed 30° C. The mixture was extracted 3 times with 50 ml of methyltertiarybutyl ether (MTB) in each case. The organic phase was then washed twice with 50 ml of H$_2$O, dried and evaporated, and the residue was purified by chromatography on silica gel in MTB/Lexane (1:1) via a frit. The fractions were then evaporated, giving 2.5 g of solid, which was recrystallized from n-heptane, giving 1.7 g of the compound 2-cyano-3-fluoro-5-(4-n-phenyl-trans-cyclohexyl) phenol

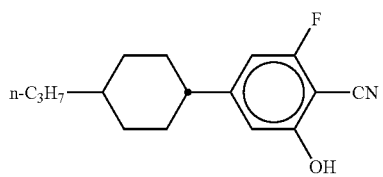

abbreviated to PCH-3N.F.OH.

The melting point was 138.6° C.

The following were prepared analogously:

Compounds 2 to 7

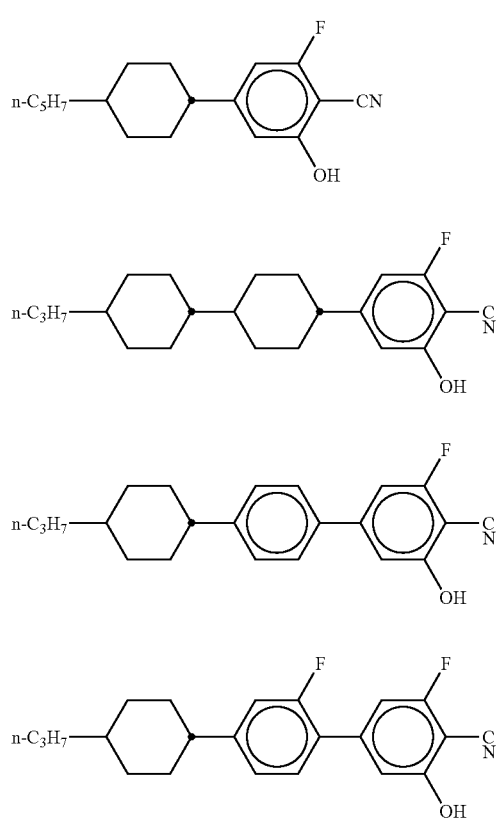

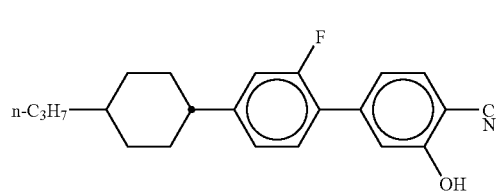

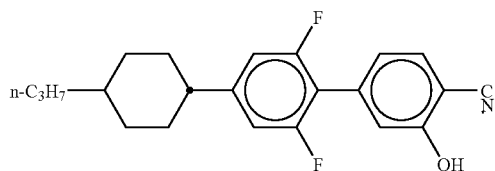

Example 2

Substance Example 2

Compound No. 8

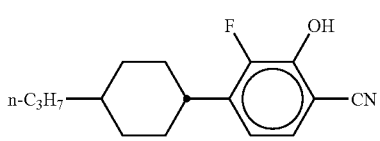

was prepared analogously to Compound 1 in Example 1 using the corresponding starting compound, in accordance with the following scheme.

Scheme 2

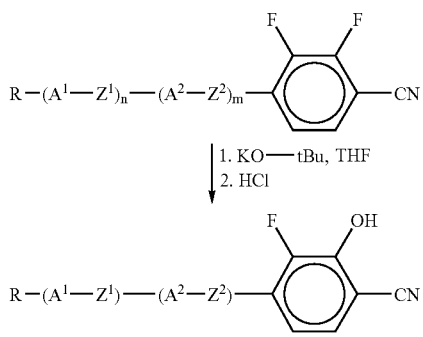

R, A$^1$, Z$^1$, A$^2$, Z$^2$, m and n are as defined above under the formula I.

Example 2a

Substance Example 3

Compound No. 9

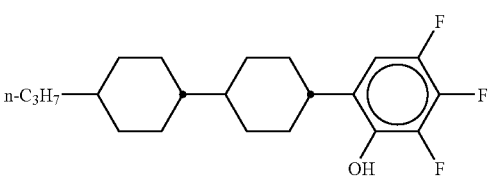

was prepared.

The physical properties are:
phase sequence C 71° C. N 83.4° I

Example 2b Substance Example 4

Compound No. 10

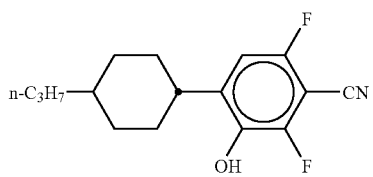

was prepared.

C 112° C. I

Example 2c

Substance Example 5

Compound No. 11 (CCP-3-CN.OH—F.F.F. for Short)

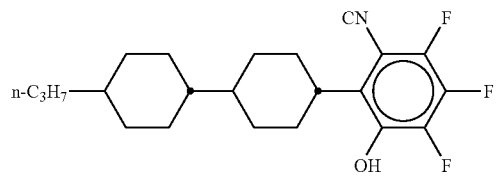

was prepared.

C 229° C. I

Example 2d

Substance Example 6

The Compound

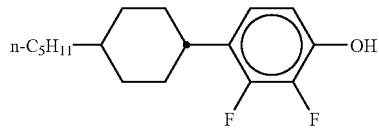

was prepared.

K 94° C. I

Example 2e

Substance Example 7

The Compound

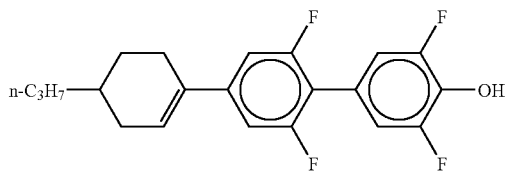

was prepared.

C 146° C. I

Example 3

Use Example 1

1000 ppm or 10,000 ppm (by weight) of the compound PLH-3N.F.OH from Example 1 were added to a liquid-crystal mixture A-0.

The composition and physical properties of the liquid-crystal mixture A-0 are shown in the table below (Table 1). The concentration data for the individual compounds, like all concentration data in this application, are by weight, unless explicitly stated otherwise.

TABLE 1

| Mixture A-0 Composition | |
|---|---|
| Substance | Concentration/% |
| PCH-3 | 13.75 |
| PCH-4 | 2.75 |
| PCH-301 | 17.00 |
| PCH-302 | 16.75 |
| PCH-304 | 13.00 |
| CH-33 | 3.25 |
| CH-35 | 3.25 |
| CH-43 | 3.25 |
| CH-45 | 3.00 |
| CBC-33F | 4.75 |
| CBC-53F | 5.50 |
| CBC-55F | 3.75 |
| CBC-33 | 4.00 |
| CBC-53 | 6.00 |

Physical Properties

| | | |
|---|---|---|
| T (N, I) | = | 96° C. |
| $\Delta n$ (589 nm) | = | 0.108 |
| $\Delta \epsilon$ (1 kHz) | = | 3.1 |
| $V_{10}$ | = | 2.8 V |

The specific resistance of mixtures A-0, A-1000 and A-10,000 were measured. The results are shown in the table below (Table 2):

TABLE 2

| Specific resistance of the liquid-crystal mixture A containing PCH-3N.F.OH | | |
|---|---|---|
| Mixture | c (dopant)/ppm | SR/Ωcm |
| A-0 | 0 | $1.4 \cdot 10^{13}$ |
| AP-1000 | 1000 | $1.1 \cdot 10^{11}$ |
| AP-10,000 | 10,000 | $1.0 \cdot 10^{11}/2.0 \cdot 10^{10}$ |

Example 4

Use Example 2

1000 ppm (by weight) of compound PCH-3N.F.OH from Example 1 were added to the liquid-crystal mixture A-0 from Example 3, and the resultant mixture A-1000 was divided into 2 parts, one of which was filtered through a Millipore filter (Teflon 40 μm) (A-1000 F).

The properties of the three mixtures A-0, A-1000 and A-1000 F thus obtained and of mixture A-10,000 from Example 3 were measured in different test cells. These test cells were produced in the test cell fabrication facility at Merck KGaA. The test cells all had a layer thickness of 6.0 µm.

Test cells having five different alignment layers were used.

These alignment layers are shown in the table below (Table 3).

TABLE 3

Summary of the alignment layers used

| Name | Type | Trade name | Manufacturer |
|---|---|---|---|
| PI-1 | Polyimide | AL-1051 | Japan Synthetic Rubber |
| PI-2 | Polyimide | CU-1523 | DuPont-Merck |
| PI-3 | Polyimide | CU-2062 | DuPont-Merck |
| PI-4 | Polyimide | LX-1400 | Hitachi |
| PI-5 | Polyimide | SE-130 | Nissan Chemicals |

The properties of the three mixtures in the test cells having the five different alignment layers are shown in the table below (Table 4). All the values given are, as in the entire application, averages of at least two individual measurements, unless otherwise stated.

TABLE 4

Physical properties of mixture A containing PCH-3N.F.OH with different alignment layers

| Mixture | A-0 | AP-1000 | AP-1000 F | AP-10,000 |
|---|---|---|---|---|
| c(dop.)/ppm | 0 | 1000/1 | 1000 | 10,000 |
| SR/Ωcm | $1.4 \cdot 10^{13}$ | $1 \cdot 10^{11}$ | $3.9 \cdot 10^{11}$ | $20 \cdot 10^{10}$ |
| Polyimide | HR (20° C.)/% | | | |
| PI-1 | 99.5 | 97.7 | 97.0 | 50 |
| PI-2 | 95.5 | 94.1 | 94.3 | 57 |
| PI-3 | 85.9 | 76 | 87.5 | 57 |
| PI-4 | 92.0 | 98.3 | 91.6 | 86.7 |
| PI-5 | 98.5 | 92.6 | 97.9 | 45 |
| Polyimide | HR(100° C.)/% | | | |
| PI-1 | 93.0 | n.d. | n.d. | n.d. |
| PI-2 | 67 | n.d. | n.d. | n.d. |
| PI-3 | 59 | n.d. | n.d. | n.d. |
| PI-4 | 61 | n.d. | n.d. | n.d. |
| PI-5 | 76 | n.d. | n.d. | n.d. |
| Polyimide | $V_{10}$/V | | | |
| PI1 | 3.0 | 3.0 | 3.0 | 2.6 |
| PI2 | 3.0 | 3.1 | 2.9 | 2.9 |
| PI3 | 2.9 | 2.8 | 2.9 | 2.8 |
| PI4 | 2.8 | 2.8 | 2.8 | 2.8 |
| PI5 | 2.8 | 2.8 | 2.9 | 2.7 |
| Polyimide | $(V_{90}/V_{10}-1)$/% | | | |
| PI1 | 43 | 44 | 43 | 43 |
| PI2 | 47 | 48 | 42 | 49 |
| PI3 | 47 | 47 | 44 | 45 |
| PI4 | 49 | 44 | 44 | 45 |
| PI5 | 45 | 47 | 46 | 47 |

Example 5

Use Example 3

Liquid-crystal mixture B-0 was prepared and divided into four parts. Compound PCH-3N.F.OH from Example 1 was added to three parts in concentrations of 100 ppm, 1000 ppm and 10,000 ppm.

The resultant three mixtures of different concentrations B-100, B-1000 and B-10,000 and the original mixture B-0, containing no PCH-3N.F.OH, were investigated with respect to their physical properties, in particular with respect to their specific resistance. The results are shown in the table below (Table 6).

The liquid-crystal mixture B-0 has the composition and physical properties shown in the table below (Table 5).

TABLE 5

Mixture B-0

Composition

| Compound | Concentration/% |
|---|---|
| CCP-2F.F.F | 6.00 |
| CCP-3F.F.F | 9.00 |
| CCP-5F.F.F | 2.00 |
| CCP-2OCF3 | 8.00 |
| CCP-3OCF3 | 6.00 |
| CCP-4OCF3 | 4.00 |
| CCP-5OCF3 | 7.00 |
| PDX-3 | 2.00 |
| PDX-4 | 8.00 |
| PDX-5 | 8.00 |
| CCZU-2-F | 3.00 |
| CCZU-3-F | 16.00 |
| CCZU-5-F | 3.00 |
| CCH-301 | 6.00 |
| CCH-303 | 6.00 |
| CCH-501 | 6.00 |

Physical Properties

| T(N, I) | = | 72° C. |
|---|---|---|
| Δn (589 nm) | = | 0.075 |
| Δε (1 kHz) | = | 10.2 |
| $V_0$ (Frederick No.) | = | 1.0 V |

The specific resistance values of mixtures B-0 to B-10,000 are shown in the table below (Table 6).

TABLE 6

Specific resistance of mixture B containing PCH-3N.F.OH

| Mixture | c(dop.)/ppm | SR (20° C.)/Ωcm | SRZ(20° C.) /Ωcm | SRZ (120° C., 1 h, 20° C.)/Ωcm |
|---|---|---|---|---|
| B-0 | 0 | $2.5 \cdot 10^{13}$ | $3.0 \cdot 10^{13}$ | $1.7 \cdot 10^{13}$ |
| BP-10 | 10 | n.d. | $4.7 \cdot 10^{13}$ | $3.0 \cdot 10^{13}$ |
| BP-100 | 100 | $1.1 \cdot 10^{11}$ | $2.4 \cdot 10^{13}$ | $2.0 \cdot 10^{13}$ |
| BP-1000 | 1000 | $1.7 \cdot 10^{10}$ | $3.8 \cdot 10^{13}$ | $4.7 \cdot 10^{12}$ |
| BP-10,000 | 10,000 | $2.3 \cdot 10^{9}$ | n.m. | n.m. |

Example 6

Use Example 4

As in Example 5, compound PCH-3N.F.OH was used, but now starting from the liquid-crystal mixture C-0. The composition and physical properties of the mixtures are shown in the table below (Table 7).

TABLE 7

Mixture C-0
Composition

| Compound | Concentration/% |
|---|---|
| CC-5-V | 20.00 |
| CC-1V-V1 | 6.00 |
| PCH-2 | 12.00 |
| PCH-3 | 8.00 |
| PCH-3N.F.F | 4.00 |
| PCH-301 | 7.00 |
| CCP-2OCF3 | 9.00 |
| CCP-3OCF3 | 8.00 |
| CCZU-2-F | 6.00 |
| CCZU-3-F | 12.00 |
| BCH-32 | 4.00 |
| CP-33F | 4.00 |

Physical Properties

| | | |
|---|---|---|
| T(N, I) | = | 67.5° C. |
| $\Delta n$ (589 nm) | = | 0.085 |
| $\Delta\epsilon$ (1 kHz) | = | 7.5 |
| Rotational viscosity | = | 74 mPa · s |
| $V_0$ (Frederick No.) | = | 1.2 V |

The specific resistance values of the mixtures are shown in the table below (Table 8).

TABLE 8

Specific resistance of mixture C

| Mixture | c (dopant)/ppm | SR (20° C.)/Ωcm |
|---|---|---|
| C-0 | 0 | $5.7 \cdot 10^{11}$ |
| CP-100 | 100 | $9.2 \cdot 10^{10}$ |
| CP-1000 | 1000 | $1.8 \cdot 10^{10}$ |
| CP-10,000 | 10,000 | $3.0 \cdot 10^{9}$ |

Example 7

Use Example 5

The liquid-crystal mixture B-0 used in Example 5 was mixed with the compound

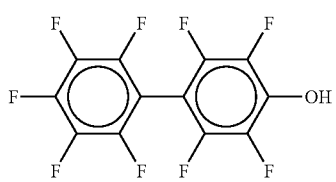

(abbreviated to BF9-OH). The melting point (transition from the crystalline phase to the isotropic phase) of this substance is 120° C. 10, 100 or 1000 μm of substance BF9-OH were added to three samples of the starting mixture B-0, and the specific resistance values of the resultant mixtures BB-10, BB-100 and BB-1000 were compared with those of the starting mixture B-0. In addition to the specific resistance values in test cells at 20° C., the specific resistance values in test cells at 20° C. after heating at 120° C. for 1 hour were also determined. The results are shown in Table 9 below.

TABLE 9

Specific resistance of mixture B containing BF9-OH

| Mixture | c(BF9-OH)/ppm | SRZ(20° C.)/Ωcm | SRZ(120° C., 1 h, 20° C.)/Ωcm |
|---|---|---|---|
| B-0 | 0 | $3.0 \cdot 10^{13}$ | $1.7 \cdot 10^{13}$ |
| BB-10 | 10 | $2.0 \cdot 10^{13}$ | $1.9 \cdot 10^{13}$ |
| BB-100 | 100 | $2.2 \cdot 10^{13}$ | $2.5 \cdot 10^{13}$ |
| BB-1000 | 1000 | $1.3 \cdot 10^{13}$ | $1.9 \cdot 10^{12}$ |

Example 8:

Use Example 6

As in Example 5, PCH-3N.F.OH was used. This was investigated in liquid-crystal mixture D-0, whose composition and properties are shown in Table 10 below.

TABLE 10

Composition of mixture D-0
Composition

| Compound | Concentration/% |
|---|---|
| CCP-2F.F.F | 5.00 |
| CCP-3F.F.F | 9.00 |
| CCP-2OCF3 | 6.00 |
| CCP-3OCF3 | 6.00 |
| CCP-4OCF3 | 5.00 |
| CCP-5OCF3 | 5.00 |
| PCH-3N.F.F | 14.00 |
| PCH-5N.F.F | 4.00 |
| CCZU-2-F | 3.00 |
| CCZU-3-F | 14.00 |
| CC-5-V | 20.00 |
| PCH-302 | 2.00 |
| CCH-35 | 4.00 |
| BCH-32 | 3.00 |

Physical Properties

| | | |
|---|---|---|
| T(N, I) | = | 70.0° C. |
| $\Delta n$ (589 nm) | = | 0.076 |
| $\Delta\epsilon$ (1 kHz) | = | 10.1 |

As in Example 7, the specific resistance values of the mixtures were measured in test cells. The results are shown in Table 11.

TABLE 11

Specific resistance of mixture D containing PCH-3N.F.OH in test cells

| Mixture | c (dopant)/ppm | SRZ (20° C.)/Ωcm | SRZ (120° C., 1 h, 20° C.)/Ωcm |
|---|---|---|---|
| D-0 | 0 | $1.2 \cdot 10^{13}$ | $1.3 \cdot 10^{13}$ |
| DP-10 | 10 | $1.2 \cdot 10^{13}$ | $1.4 \cdot 10^{13}$ |
| DP-100 | 100 | $8.4 \cdot 10^{12}$ | $8.0 \cdot 10^{12}$ |
| DP-1000 | 1000 | $2.1 \cdot 10^{11}$ | $4.0 \cdot 10^{11}$ |

Example 9:

Use Example 7

As in Example 8, liquid-crystal mixture D was used, but BF9-OH was now added, as in Example 2. The results of the specific resistance in test cells are shown in Table 12 below.

TABLE 12

Specific resistance of mixture D containing BF9-OH

| Mixture | c (dopant)/ppm | SRZ (20° C.)/Ωcm | SRZ (120° C., 1 h, 20° C.)/Ωcm |
|---|---|---|---|
| D-0 | 0 | $1.2 \cdot 10^{13}$ | $1.3 \cdot 10^{11}$ |
| DB-10 | 10 | $1.1 \cdot 10^{13}$ | $1.0 \cdot 10^{13}$ |
| DB-100 | 100 | $3.6 \cdot 10^{12}$ | $4.2 \cdot 10^{12}$ |
| DB-1000 | 1000 | $4.1 \cdot 10^{11}$ | $4.4 \cdot 10^{11}$ |

Example 10: Use Example 8

As in Example 8, mixture D-0 was used, but compound No. 11 of Example 2c (Substance Example 5)

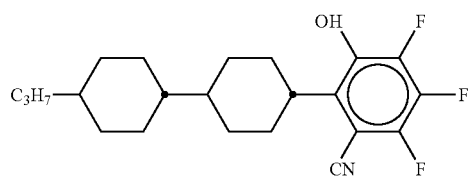

CCP-3-CN.OH—F.F.F for short, was now employed. The results for the specific resistance values in test cells are shown in Table 13 below.

TABLE 13

Specific resistance of mixture D containing CCU-3-CN.OH—F

| Mixture | c (dopant)/ppm | SRZ (20° C.)/Ωcm | SRZ (120° C., 1 h, 20° C.)/Ωcm |
|---|---|---|---|
| D-0 | 0 | $1.2 \cdot 10^{13}$ | $1.3 \cdot 10^{13}$ |
| DU-10 | 10 | $2.3 \cdot 10^{13}$ | $2.5 \cdot 10^{13}$ |
| DU-100 | 100 | $1.9 \cdot 10^{13}$ | $2.1 \cdot 10^{13}$ |
| DU-1000 | 1000 | $1.1 \cdot 10^{13}$ | $1.5 \cdot 10^{13}$ |

The acidity of the compound CCU-3-CN.OH-G is apparently at the limit of the values to be employed and is just sufficient for some applications.

Comparative Example 1

In each case, 1000 ppm of 4-cyano-4'-hydroxybiphenyl,

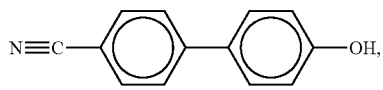

OCB for short, of various origin and pretreatment were added to liquid-crystal mixture A-0 from Example 3. The corresponding mixtures were divided, and in each case one part was filtered as described in Example 4 and in one case repeatedly filtered. The table below (Table 14) shows the results for the resistance measurements.

TABLE 14

Resistance of mixture A containing OCB

| Mixture | Origin of the OCB | c (OCB)/ppm | No. of filtrations | SR/Ω cm |
|---|---|---|---|---|
| A-0 | — | 0 | 0 | $2.7 \cdot 10^{13}$ |
| AM1-1000 | Merck KGaA 1 (recrystallized) | 1000 | 0 | $3.9 \cdot 10^{10}$ |
| AM1-1000 F | | 1000 | 1 | $2.2 \cdot 10^{11}$ |
| AM2-1000 F | Merck KGaA 2 (chromatographed) | 1000 | 0 | $1.1 \cdot 10^{11}$ |
| AM2-1000 F | | 1000 | 1 | $1.9 \cdot 10^{12}$ |
| AA-1000 | Aldrich (chromatographed) | 1000 | 0 | $5.3. \cdot 10^{11}$ |
| AA-1000 F | | 1000 | 1 | $4.4 \cdot 10^{12}$ |
| AA-1000 | | 1000 | 0 | $2.0 \cdot 10^{12}$ |
| AA-1000 F | | 1000 | 1 | $1.6 \cdot 10^{12}$ |
| AA-1000 FF | | 1000 | 2 | $5.2 \cdot 10^{12}$ |
| AA-1000 FFF | | 1000 | 3 | $6.5 \cdot 10^{12}$ |

As can be seen from Table 14, although the compound OCB is suitable for reducing the resistance of liquid-crystal mixtures, the results are, however, unreproducible. Firstly, the results depend on the origin and pre-history (for example the purification method) of the OCB, and secondly, the results change significantly if the mixtures are subjected to standard operations, for example filtration.

Comparative Example 2

Various amounts of 2,6-bis-tert-butyl-4-(4-n-propyltrans-cyclohexyl)phenol

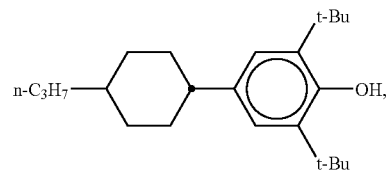

TBCP for short, were added to liquid-crystal mixture E-0.
Mixture E-0 has the composition shown below (Table 15) and has the properties described therein.

TABLE 15

Mixture E–O Composition

| Compound | Concentration/% |
|---|---|
| PCH-5F | 10.00 |
| PCH-6F | 8.00 |
| PCH-7F | 6.00 |
| CCP-20CF3 | 8.00 |
| CCP30CF3 | 12.00 |
| CCP-40CF3 | 7.00 |
| CCP-50CF3 | 11.00 |
| BCH-3F.F | 12.00 |
| BCH.5F.F | 10.00 |
| ECCP-30CF3 | 5.00 |
| ECCP-50CF3 | 5.00 |

TABLE 15-continued

Mixture E–O Composition

| Compound | Concentration/% |
|---|---|
| CBC-33F | 2.00 |
| CBC-53F | 2.00 |
| CBF-55F | 2.00 |

Physical Properties

| | |
|---|---|
| $T(N, 5) =$ | 92° C. |
| $\Delta n$ (589 nm) = | 0.097 |
| $\Delta\epsilon$ (1 kHz) = | 5.2 |
| $V_{10} =$ | 2.0 V |

For the mixtures having the various concentrations, the voltage holding ratio was determined as in Example 4. The alignment layer here was PI-1 (AL-1051 from Japan Synthetic Rubber). The results are shown in the table below (Table 16).

TABLE 16

Voltage holding ratio for mixture E Containing TBCP

| Mixture | C (TBCP)/ppm | HR (20° C.)/% |
|---|---|---|
| E-0 | 0 | 99.7 |
| ET-1000 | 1000 | 97.6 |
| ET-2500 | 2500 | 97.4 |
| ET-5000 | 5000 | 96.8 |

As can be seen from the results in Table 11, the compound TBCP is not suitable for reducing the specific resistance or voltage holding ratio of liquid-crystal mixtures. This is probably due to its low $pK_a$ value, i.e. its low acidity.

Comparative Example 3

Various concentrations of the compound 4-cyano-3-fluorophenol,

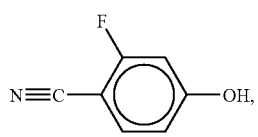

CFP for short, were dissolved in liquid-crystal mixture A from Example 3, giving the specific resistance values shown in the table below

TABLE 17

Specific resistance of mixture A containing CFP

| Mixture | c (CFP)/ppm | SR/Ω cm |
|---|---|---|
| A-0 | 0 | $1.2 \cdot 10^{13}$ |
| ACF-1 | 1 | $5.3 \cdot 10^{12}$ |
| ACF-10 | 10 | $2.7 \cdot 10^{12}$ |

TABLE 17-continued

Specific resistance of mixture A containing CFP

| Mixture | c (CFP)/ppm | SR/Ω cm |
|---|---|---|
| ACF-100 | 100 | $8.3 \cdot 10^{11}$ |
| ACF-1000 | 1000 | $1.0 \cdot 10^{11}$ |
| ACF-5000 | 5000 | $1.3 \cdot 10^{10}$ |
| ACF-10,000 | 10,000 | $4.8 \cdot 10^{9}$ |

As can be seen from the results in Table 12, the compound CFP, which has a relatively high $pK_a$ value, can be used to reduce the specific resistance of liquid-crystal mixtures. The voltage holding ratio was then determined in liquid-crystal cells containing PI-1. The results are shown in Table 18.

TABLE 18

Voltage holding ratio of mixture A containing CFP

| Mixture | c (CFP)/% | HR (20° C.)/% | HR (100° C.)/% |
|---|---|---|---|
| D-0 | 0 | 99.7 | 98.6 |
| A-0 | 0 | 98.8 | 87.9 |
| ACF-1 | 1 | 99.4 | 89.1 |
| ACF-10 | 10 | 99.4 | 89.2 |
| ACF-100 | 100 | 98.4 | 86.8 |

It can be seen that, particularly at low CFP concentrations, there is at best a small effect, if any at all. Furthermore, samples were investigated after various storage times and after various times in opened containers under nitrogen gas and after various times in the vacuum cell-filling unit. It was found that the resistance of the mixtures containing CFP increases significantly in particular on storage in open containers under nitrogen and very particularly in the vacuum filling unit, and the voltage holding ratio likewise increases. This behaviour can probably be attributed to the high vapour pressure of the compound CFP. This makes it unsuitable for practical use, although, as shown in Table 12, it does in some cases have the desired effect on the resistance of liquid-crystal mixtures.

Comparative Example 4

Analogously to Comparative Example 3, the compound 4-ethoxy-3-cyano-2-fluorophenol,

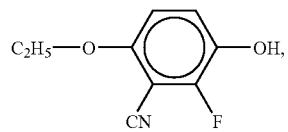

ECFP for short, was investigated in the liquid-crystal mixture A-0. Very similar results were obtained. Like CFP, ECFP also results in a significant reduction in the specific resistance which is clearly dependent on the concentration employed. The effect is somewhat greater in the case of ECFP than in the case of CFP. However, the problem of the excessive vapour pressure also occurs for ECFP, albeit to a somewhat lesser extent than for CFP. Like CFP, ECFP is therefore not particularly suitable for practical applications.

Comparative Example 5

The compound 2-cyano-4-(4-n-propyl-trans-cyclohexyl) phenol,

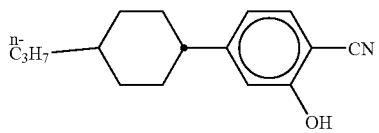

PCH-3N.OH, prepared analogously to the compound PCH-3N.F.OH in Example 1, has a melting point of 145.4° C. As in Example 3, the specific resistance of PCH-3N.OH was determined in mixture A-0. The results are shown in Table 19.

TABLE 19

| Specific resistance of mixture A containing PCH-3N.OH | | |
|---|---|---|
| Mixture | c (PCH-3N.OH)/ppm | SR/Ωcm |
| A-0 | 0 | $1.4 \cdot 10^{13}$ |
| AN-1000 | 1000 | $1.0 \cdot 10^{12}$ |

Compared to Example 3(Table 2, mixture A-1000), it can be seen that 1000 ppm of PCH-3N.F.OH reduce the specific resistance of mixture A-0 only from $1.9 \cdot 10^{13}$ Ωcm to $1.0 \cdot 10^{12}$ Ωcm, whereas the compound of Example 1, PCH-3N.OH, in the same concentration reduces the specific resistance to $1.0 \cdot 10^{11}$ Ωcm. Owing to the lower acidity compared with PCH-3N.F.OH, PCH-3N.OH is therefore not as suitable for adjusting the specific resistance of liquid-crystal mixtures, such as mixture A-0.

Comparative Example 6

As in Example 8, mixture D-0 was used. Now, however, the compound

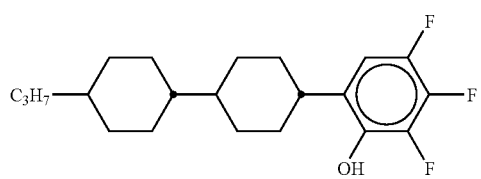

CCP-3OH-F.F.F for short, was employed. The results for the specific resistance values in the test cells are shown in Table 20 below.

TABLE 20

| Resistance of mixture D containing CCP-3OH-F.F.F | | | |
|---|---|---|---|
| Mixture | c (dopant)/ ppm | SRZ (20° C.)/ Ωcm | SRZ (120° C., 1 h, 20° C.)/ Ωcm |
| D-0 | 0 | $1.2 \cdot 10^{13}$ | $1.3 \cdot 10^{13}$ |
| DC-10 | 10 | $9.8 \cdot 10^{12}$ | $1.1 \cdot 10^{13}$ |
| DC-100 | 100 | $1.4 \cdot 10^{13}$ | $1.2 \cdot 10^{13}$ |
| DC-1000 | 1000 | $8.7 \cdot 10^{12}$ | $1.1 \cdot 10^{13}$ |

As can be seen from the results, the compound CCP-3OH-F.F.F is not suitable for adjusting the resistance. This seems to be attributable to its inadequate $pK_a$ value.

Comparative Example 7

As in Example 8, mixture D-0 was used. Now, however, the compound added was

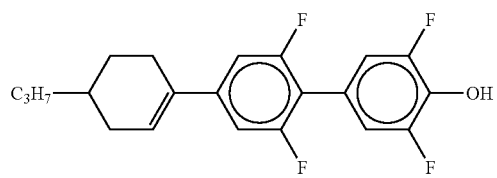

LUU-3-OH for short, was employed. The results are shown in Table 21 below.

TABLE 21

| Resistance of mixture D containing LUU-3-OH | | | |
|---|---|---|---|
| Mixture | c (dopant)/ ppm | SRZ (20° C.)/ Ωcm | SRZ (120° C., 1 h, 20° C.)/ Ωcm |
| D-0 | 0 | $1.2 \cdot 10^{13}$ | $1.3 \cdot 10^{13}$ |
| DL-10 | 10 | $1.9 \cdot 10^{13}$ | $2.0 \cdot 10^{13}$ |
| DL-100 | 100 | $2.2 \cdot 10^{13}$ | $2.0 \cdot 10^{13}$ |
| DL-1000 | 1000 | $1.7 \cdot 10^{13}$ | $1.6 \cdot 10^{13}$ |

Like dopant CCP-3OH-F.F.F from Comparative Example 6, LUU-3-OH is also unsuitable for adjusting the resistance.

The entire disclosure of all applications, patents and publications, cited above, and of corresponding German application Nos. 198 04 300.7 filed Feb. 4, 1998, 198 05 912.4 filed Feb. 13, 1998 and 198 51 805.6 filed Nov. 11, 1998 are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the following formula

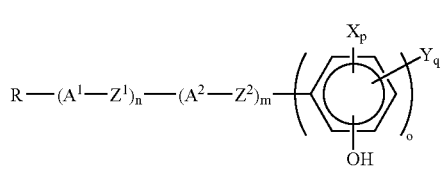

Ib wherein
$A^1$ and $A^2$ are each, independently of one another, and in the case where $A^1$ occurs a number of times, each $A^1$ is independently of the others:
a) 1,4-cyclohexylene or trans-1,4-cyclohexenylene, in which optionally one or more non-adjacent $CH_2$ groups are replaced by O and/or S, b) 1,4-phenylene, in which optionally one or two CH groups are replaced by N,
or
c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl, in which (a) and (b) are, independently, unsubstituted, monosubstituted or disubstituted by F atoms, $Z^1$ and $Z^2$ are each, independently of one another, and in the case where $Z^1$ occurs a number of times, each $Z^1$ is independently of the others, —CO—O—, —O—CO—, —CO—CH$_2$—, —CH$_2$—CO—, —CH$_2$O—, —OCH$_2$—, —CH$_2$CH$_2$—, —CH=CH—, —C/C— or a single bond, or one of the groups $Z^1$ and $Z^2$ is —(CH$_2$)$_4$—, —(CH$_2$)$_3$CO—, —(CH$_2$)$_2$—O—CO—, —(CH$_2$)$_2$—(CO—O)—, CH=CH—CH$_2$CH$_2$—, —CH$_2$CH$_2$—CH=CH— or —CH$_2$—CH=CH—CH$_2$—, R is H, CN, F, Cl, COOR=, or OH, or alkyl or alkenyl having 1 to 15 or 2 to 15 carbon atoms, respectively, which are unsubstituted, monosubstituted by CN or CF$_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, R= is H, or alkyl or alkenyl having 1 to 15 or 2 to 15 carbon atoms, respectively, which are unsubstituted, monosubstituted by CN or CF$_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, n is 0, 1 or 2,
m is 0 or 1,
o is 1, 2 or 3,
n+m+o is 2, 3 or 4,
X and Y are each, independently of one another, including the case where X and Y occur a number of times, F, Cl, COOR', NO$_2$ or CN,
p is 0, 1, 2, or 3, and
q is 0, 1, 2, or 3,
and wherein at least one of the following conditions a) and/or b) is fulfilled:
a) one of all substituents X and Y, which are present, is CN, and p+q is 2 or more, and/or
b) o is 2 or 3 and five or more of all substituents X and Y, which are present, are F;
or I) a compound of one of the following formulae

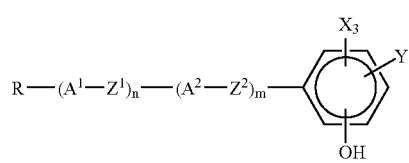
Ia-6

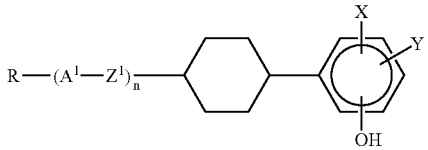
Ib-1

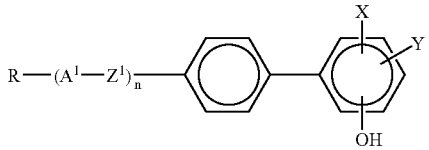
Ib-2

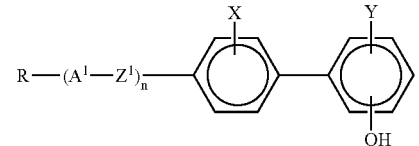
Ib-3

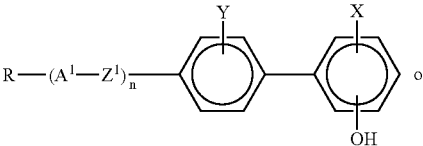
Ib-4

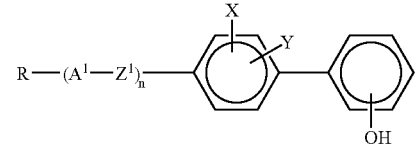
Ib-5 wherein
$A^1$, $A^2$, $Z^1$, $Z^2$, R, n, m, and X are as defined previously and Y is CN;
or II) a compound of one of the following formulae

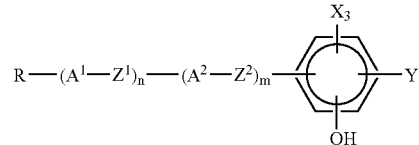
Ia-6

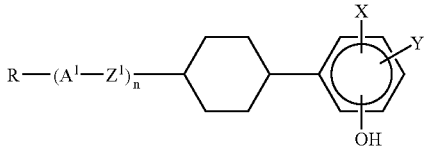
Ib-1

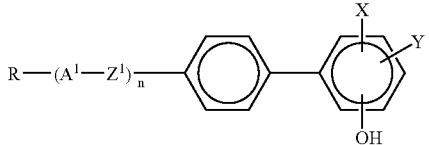
Ib-2

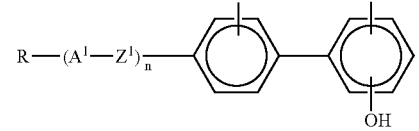
Ib-3

-continued

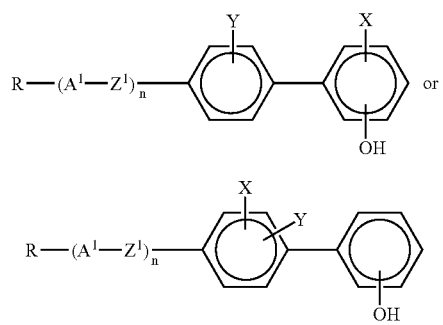

wherein
A¹, A², Z¹, Z², R, n, m, and X are as defined previously, and Y is CN and X is not F; or III) a compound of one of the following formulae

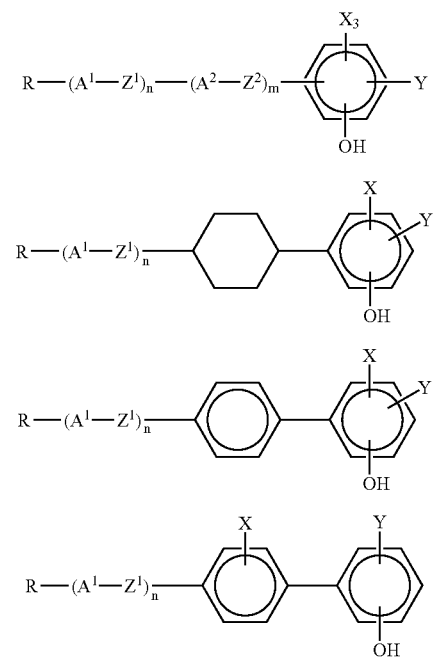

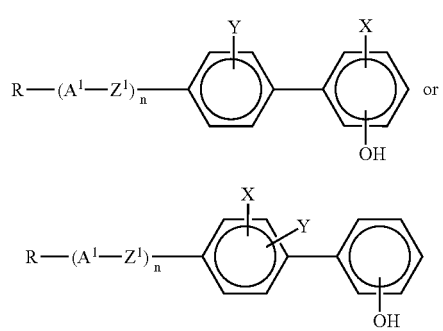

wherein
A¹, A², Z¹, Z², R, n and m, are as defined previously, Y is CN, and X is F; or IV) a compound of one of the following formulae

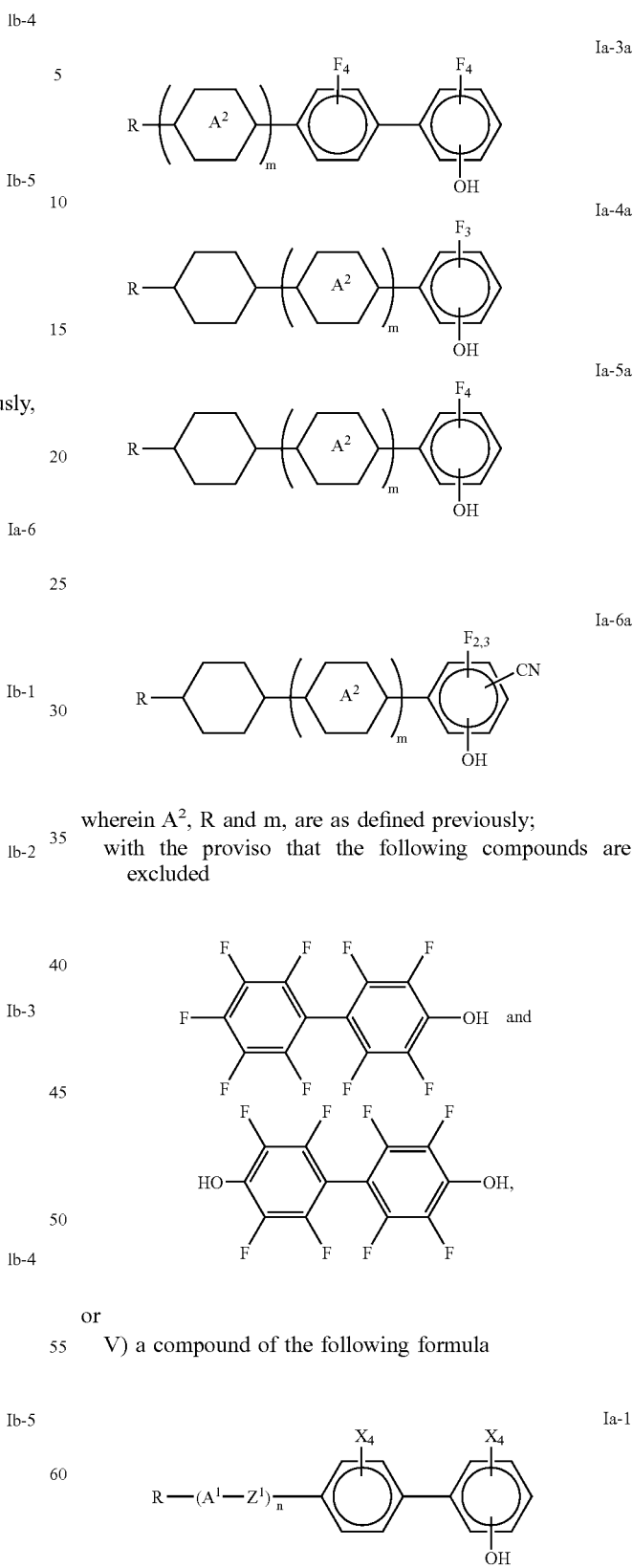

wherein $A^2$, R and m, are as defined previously;
with the proviso that the following compounds are excluded or V) a compound of the following formula wherein
$A^1$, $Z^1$, R, n, and X are as defined previously;

with the proviso that the following compounds are excluded

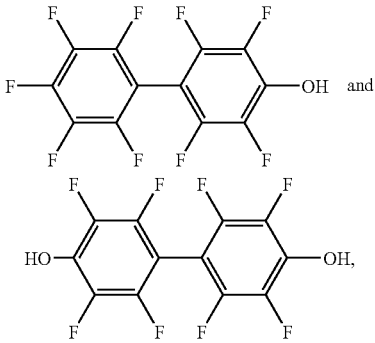

or

VI) a compound of one of the following formulae

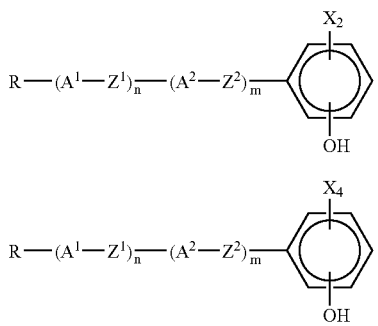
Ia-4

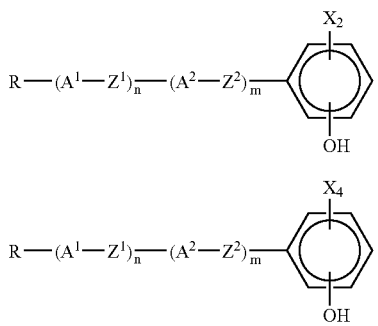
Ia-5 wherein $A^1$ $A^2$, $Z^1$, $Z^2$, n, m, and R are as defined previously, and wherein X is F and in formula 1a-4 at least one of the rings $A^1$ and $A^2$ is present and at least one of the rings $A^1$ and $A^2$ which is present, is substituted at least once by an F-atom and in formula 1a-5 at least one of the rings $A^1$ and $A^2$, is present, and at least one of the rings $A^1$ and $A^2$ which is present is substituted at least twice, once by an F-atom, or at least two of the rings $A^1$ and $A^2$ are present and at least two of the rings $A^1$ and $A^2$, which are present, are substituted at least twice by an F-atom;

with the proviso that the following compounds are excluded

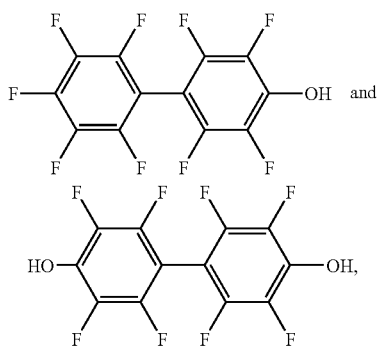

or

VII) a compound of formula 1 a-5a

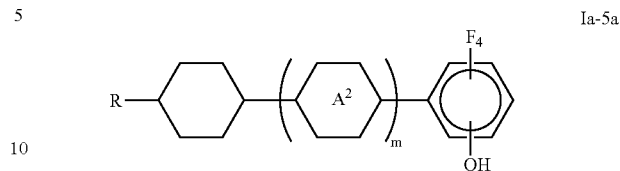
Ia-5a wherein $A^2$, R, and m are as defined, and wherein at least one of the rings $A^2$ which is present is a phenyl ring, which is substituted at least once by F.

2. A compound according to claim 1, which is a compound of one of the following formulae

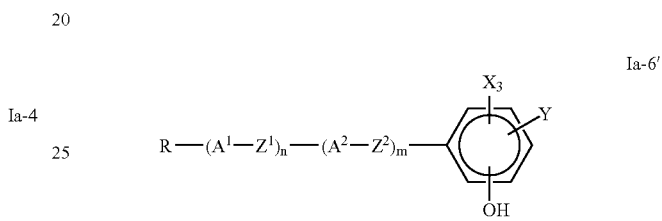
Ia-6'

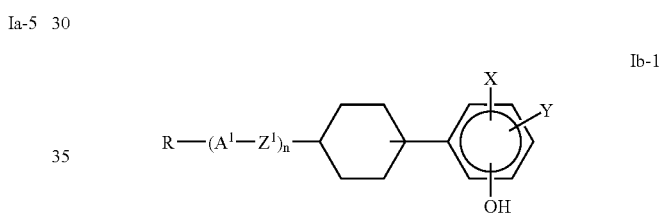
Ib-1

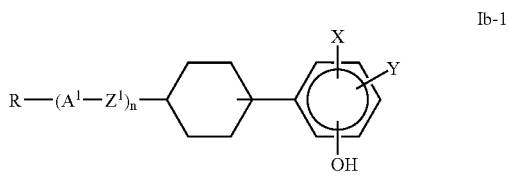
Ib-2

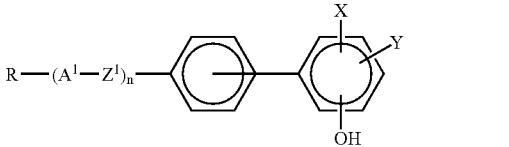
Ib-3

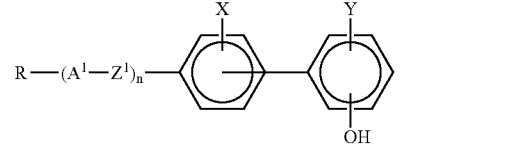
Ib-4 or

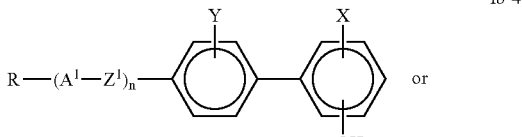
Ib-5

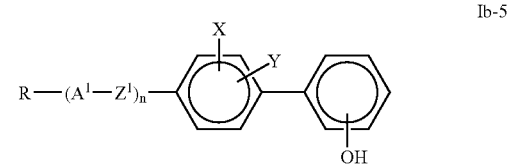

wherein $A^1$, $A^2$, $z^1$, $Z^2$, R, n, m, and X are as defined in claim 1, and Y is CN, or
a compound of one of the following formulae

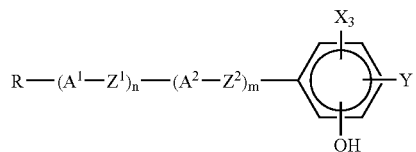
Ia-6

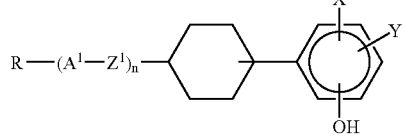
Ib-1

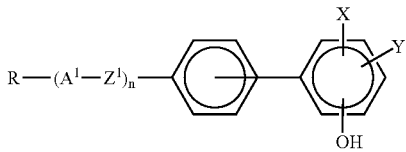
Ib-2

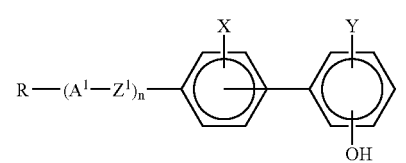
Ib-3

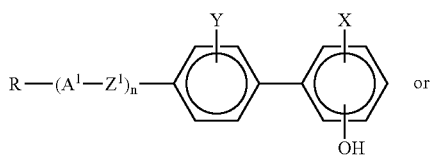
Ib-4

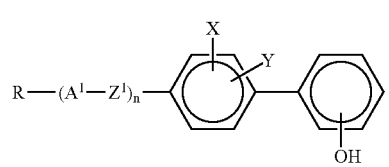
Ib-5 wherein
$A^1$, $A^2$, $Z^1$, $Z^2$, R, n, m, and X are as defined in claim 1, and Y is CN and X is not F, or
a compound of one of the following formulae

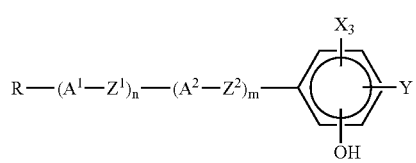
Ia-6

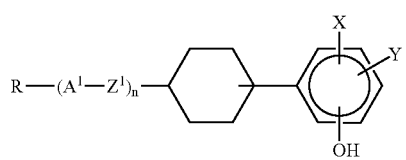
Ib-1

-continued

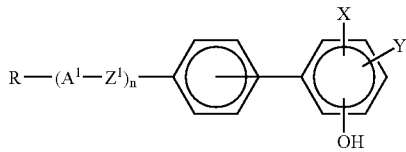
Ib-2

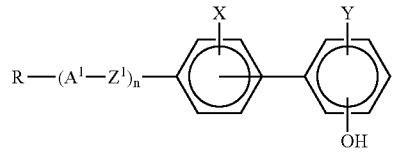
Ib-3

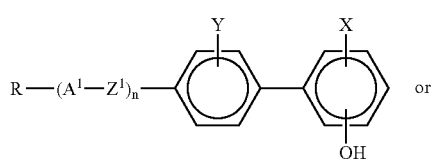
Ib-4 or

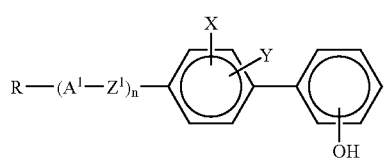
Ib-5 wherein
$A^1$, $A^2$, $Z^1$, $Z^2$, R, n and m, are as defined in claim 1, Y is CN, and X is F,
or
a compound of one of the following formulae

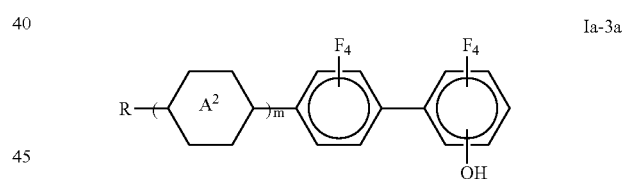
Ia-3a

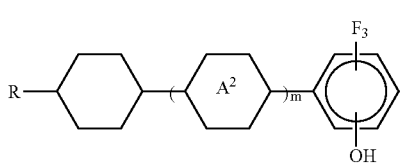
Ia-4a

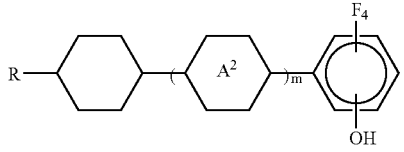
Ia-5a

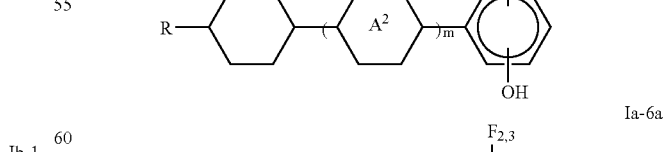
Ia-6a wherein $A^2$, R and m, are as defined in claim 1, or
a compound of the following formula

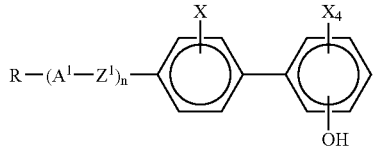
Ia-1 wherein
$A^1, Z^1$, R, n, and X are as defined in claim 1,
or
a compound of one of the following formulae

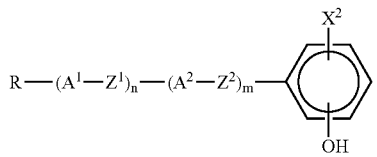
Ia-4

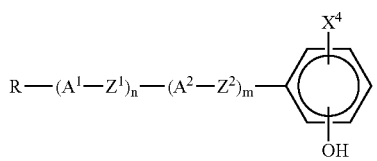
Ia-5 wherein
$A^1, A^2, z^1, Z^2$, n, m, and R are as defined in claim 1, and
wherein X is F and in formula Ia-4 at least one of the rings $A^1$ and $A^2$ is present and at least one of the rings $A^1$ and $A^2$ which is present, is substituted at least once by an F-atom and in formula Ia-5 at least one of the rings $A^1$ and $A^2$, is present, and at least one of the rings $A^1$ and $A^2$ which is present is substituted at least twice, once by an F-atom, or at least two of the rings $A^1$ and $A^2$ are present and at least two of the rings $A^1$ and $A^2$, which are present, are substituted at least twice by an F-atom,
or
a compound of formula Ia-5a

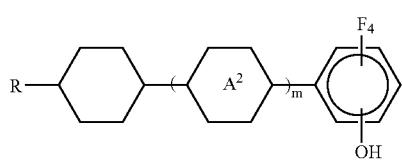
Ia-5a wherein
$A^2$, R, and m are as defined in claim 1, and
wherein at least one of the rings $A^2$ which is present is a phenyl ring, which is substituted at least once by F,
with the proviso that the following compounds are excluded

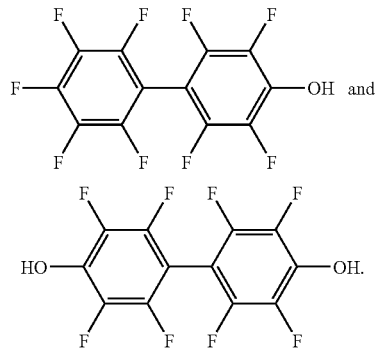

3. A compound according to claim 1, which is of one of the following formulae

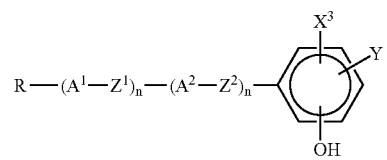
Ib-1

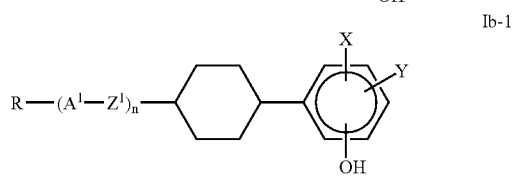
Ib-2

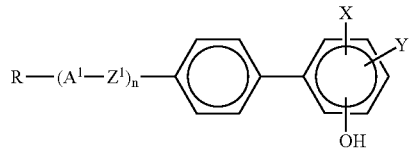
Ib-3

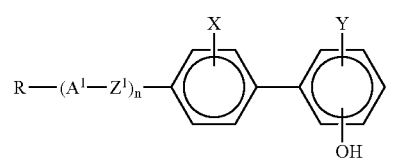
Ib-4 or

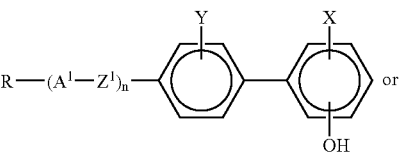
Ib-5 wherein
$A^1, A^2, Z^1, Z^2$, R, n, m, and X are as defined in claim 1 and Y is CN.

4. A compound according to claim 1, which is of one of the following formulae

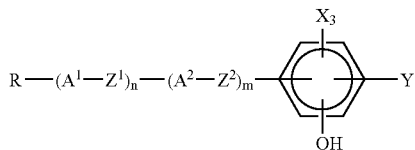
Ia-6

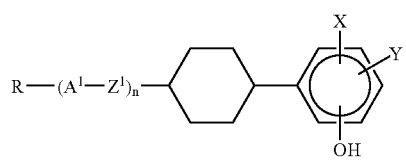
Ia-1

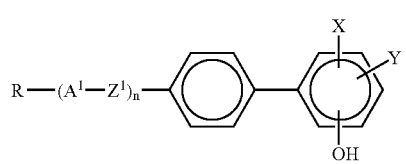
Ib-2

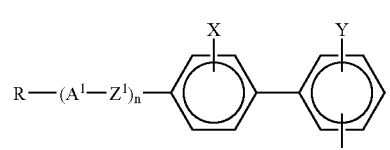
Ib-3

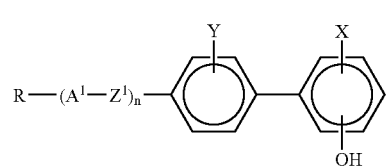
Ib-4

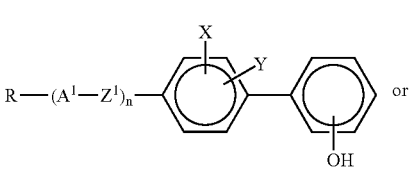
Ib-5 or wherein $A^1$, $A^2$, $Z^1$, $Z^2$, R, n, m, and X are as defined in claim 1, and Y is CN and X is not F.

5. A compound according to claim 1, which is of one of the following formulae

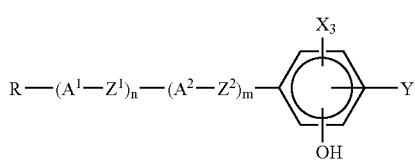
Ia-6

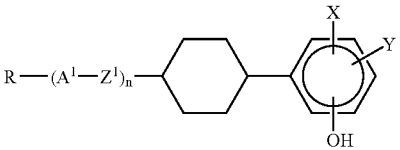
Ia-1

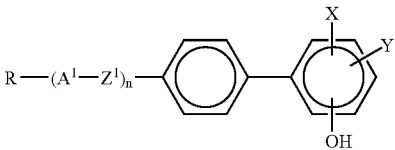
Ib-2

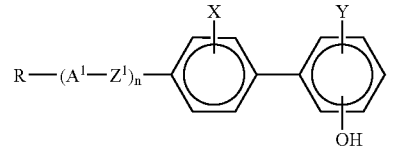
Ib-3

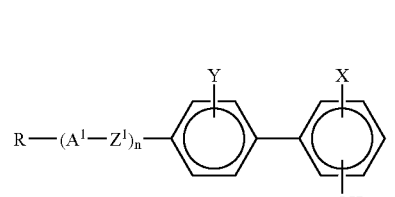
Ib-4

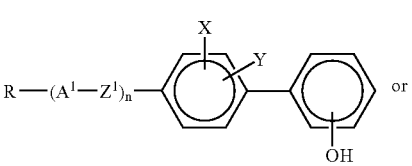
Ib-5 or wherein $A^1$, $A^2$, $Z^1$, $Z^2$, R, n and m, are as defined in claim 1, Y is CN, and X is F.

6. A compound according to claim 1, which is of one of the following formulae

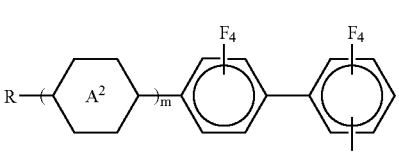
Ia-3a

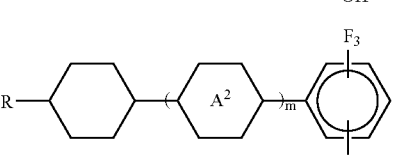
Ia-4a

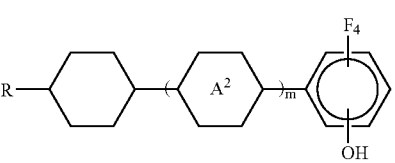
Ia-5a

7. A compound according to claim 1, which is of the following formula

Ia-1 wherein
A$^1$, Z$^1$, R, n, and X are as defined in claim 1, with the proviso that the following compounds are excluded

8. A compound according to claim 1, which is of one of the following formulae Ia-4

Ia-5 wherein A$^1$, A$^2$, Z$^1$, Z$^2$, n, m, and R are as defined in claim 1, and wherein X is F and in formula Ia-4 at least one of the rings A$^1$ and A$^2$ is present and at least one of the rings A$^1$ and A$^2$ which is present, is substituted at least once by an F-atom and in formula Ia-5 at least one of the rings A$^1$ and A$^2$, is present, and at least one of the rings A$^1$ and A$^2$ which is present is substituted at least twice, once by an F-atom, or at least two of the rings A$^1$ and A$^2$ are present and at least two of the rings A$^1$ and A$^2$, which are present, are substituted at least twice by an F-atom, with the proviso that the following compounds are excluded

9. A compound according to claim 1, which is of formula Ia-5a wherein

Ia-5a

A$^2$, R, and m are as defined in claim 1, and
wherein at least one of the rings A$^2$ which is present is a phenyl ring, which is substituted at least once by F.

10. A compound of formula Ia' of claim 1, wherein one of all substituents X and Y, which are present, is CN, and p+q is 2 or more.

11. A compound of formula Ia' of claim 1, wherein o is 2 or 3 and five or more of all substituents X and Y, which are present, are F.

12. A method of using a compound of formula Ia'

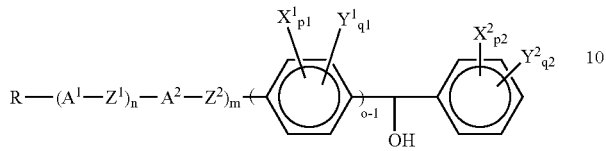

in which
  $A^1$ and $A^2$ are each, independently of one another, and in the case where $A^1$ occurs a number of times, each $A^1$ is independently of the others:
  a) 1,4-cyclohexylene or trans-1,4-cyclohexenylene, in which optionally one or more non-adjacent $CH_2$ groups are replaced by O and/or S,
  b) 1,4-phenylene, in which optionally one or two CH groups are replaced by N,
  or
  c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
  in which (a) and (b) are, independently, unsubstituted, monosubstituted or disubstituted by F atoms,
  $Z^1$ and $Z^2$ are each, independently of one another, and in the case where $Z^1$ occurs a number of times, each $Z^1$ is independently of the others,
    —CO—O—, —O—CO—, —CO—$CH_2$—, —$CH_2$—CO—, —$CH_2O$—, —$OCH_2$—, —$CH_2CH_2$—, —CH=CH—, —C/C— or a single bond, or
  one of the groups $Z^1$ and $Z^2$ is
    —$(CH_2)_4$—, —$(CH_2)_3$CO—, —$(CH_2)_2$—O—CO—, —$(CH_2)_2$—(CO—O)—, CH=CH—$CH_2CH_2$—, —$CH_2CH_2$—CH=CH— or —$CH_2$—CH=CH—$CH_2$—,
  R is H, CN, F, Cl, COOR=, or OH, or alkyl or alkenyl having 1 to 15 or 2 to 15 carbon atoms, respectively, which are unsubstituted, monosubstituted by CN or $CF_3$ or monosubstituted or polysubstituted by halogen, in which one or more $CH_2$ groups are optionally replaced, independently of one another, by —O—, —S—, -◊- —CO—, —CO—O—, —O—CO— or —O—CO—O— in such a way that O atoms are not bonded directly to one another,
  R= is H, or alkyl or alkenyl having 1 to 15 or 2 to 15 carbon atoms, respectively, which are unsubstituted, monosubstituted by CN or $CF_3$ or monosubstituted or polysubstituted by halogen, in which one or more $CH_2$ groups are optionally replaced, independently of one another, by —O—, —S—, -◊- —CO—, —CO—O—, —O—CO— or —O—CO—O— in such a way that O atoms are not bonded directly to one another,
  n is 0, 1 or 2,
  m is 0 or 1,
  o is 1, 2 or 3,
  n+m+o is 2, 3 or 4,
  $X^1$, $X^2$, $Y^1$, and $Y^2$ are each, independently of one another, including the case where $X^1$, $X^2$, $Y^1$ and/or $Y^2$ occur a number of times, F, Cl, COOR', $NO_2$ or CN, and
  $p_1$, $P_2$, $q_1$ and $q_2$ are each 0, 1, 2, 3 or 4, and wherein one of the following conditions is fulfilled
  the compound of formula Ia' has five or more fluorine-substituents in the phenolic moiety, or
  the compound of formula Ia' has one CN group in the phenolic moiety, subject to the proviso that compounds of the formulae A and B are excluded

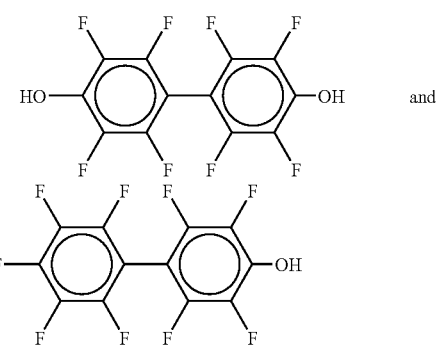

comprising incorporating said compound of formula Ia' into a liquid-crystal display.

13. A liquid-crystal display containing a compound of formula Ia'

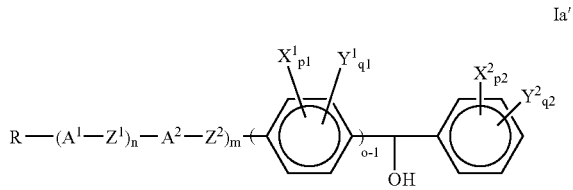

in which
  $A^1$ and A2 are each, independently of one another, and in the case where $A^1$ occurs a number of times, each $A^1$ is independently of the others:
  a) 1,4-cyclohexylene or trans-1,4-cyclohexenylene, in which optionally one or more non-adjacent $CH_2$ groups are replaced by O and/or S,
  b) 1,4-phenylene, in which optionally one or two CH groups are replaced by N,
  or
  c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
  in which (a) and (b) are, independently, unsubstituted, monosubstituted or disubstituted by F atoms,
  $Z^1$ and $Z^2$ are each, independently of one another, and in the case where $Z^1$ occurs a number of times, each $Z^1$ is independently of the others,
    —CO—O—, —O—CO—, —CO—$CH_2$—, —$CH_2$—CO—, —$CH_2O$—, —$OCH_2$—, —$CH_2CH_2$—, —CH=CH—, —C/C— or a single bond, or
  one of the groups $Z^1$ and $Z^2$ is
    —$(CH_2)_4$—, —$(CH_2)_3$CO—, —$(CH_2)_2$—O—CO—, —$(CH_2)_2$—(CO—O)—, CH=CH—$CH_2CH_2$—, —$CH_2CH_2$—CH=CH— or —$CH_2$—CH=CH—$CH_2$—,
  R is H, CN, F, Cl, COOR=, or OH, or alkyl or alkenyl having 1 to 15 or 2 to 15 carbon atoms, respectively, which are unsubstituted, monosubstituted by CN or $CF_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, R is H, or alkyl or alkenyl having 1 to 15 or 2 to 15 carbon atoms, respectively, which are unsubstituted, monosubstituted by CN or CF$_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, n is 0, 1 or 2, m is 0 or 1, o is 1, 2 or 3, n+m+o is 2, 3 or 4, $X^1$, $X^2$, $Y^1$, and $Y^2$ are each, independently of one another, including the case where $X^1$, $X^2$, $Y^1$ and/or $Y^2$ occur a number of times, F, Cl, COOR', NO$_2$ or CN, and $p_1$, $p_2$, $q_1$ and $q_2$ are each 0, 1, 2, 3 or 4, and wherein one of the following conditions is fulfilled the compound of formula Ia' has five or more fluorine-substituents in the phenolic moiety, or the compound of formula Ia' has one CN group in the phenolic moiety, subject to the proviso that compounds of the formulae A and B are excluded

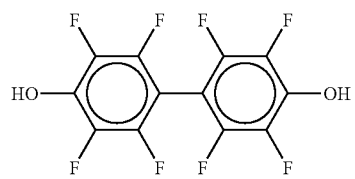

A

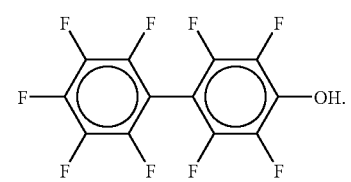

B

14. A liquid-crystal display according to claim 13, said display being an STN, AMD, TN or IPS display.

15. A method of adjusting the specific resistance of a liquid-crystal mixture, comprising adding an acidic compound to the liquid-crystal mixture, wherein the acidic compound is a mesogenic compound that has a vapor pressure as low or lower than the compound of formula C

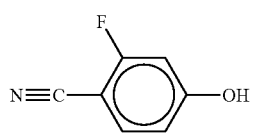

and simultaneously has an acidity measured in pk$_a$ that is as high as or higher than that of the compound of formula D

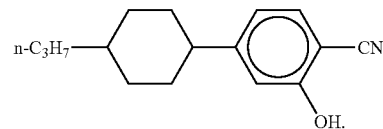

16. A method of adjusting the specific resistance of liquid-crystal mixtures, comprising adding to the liquid crystal mixture a compound of formula Ia'

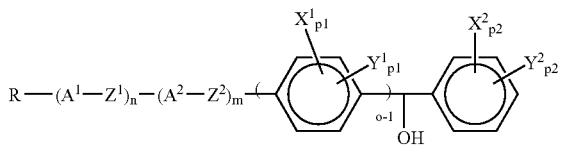

Ia' in which
A$^1$ and A$^2$ are each, independently of one another, and in the case where A$^1$ occurs a number of times, each A$^1$ is independently of the others:
a) 1,4-cyclohexylene or trans-1,4-cyclohexenylene, in which optionally one or more non-adjacent CH$_2$ groups are replaced by O and/or S,
b) 1,4-phenylene, in which optionally one or two CH groups are replaced by N,
or
c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl,
in which (a) and (b) are, independently, unsubstituted, monosubstituted or disubstituted by F atoms, Z$^1$ and Z$^2$ are each, independently of one another, and in the case where Z$^1$ occurs a number of times, each Z$^1$ is independently of the others,
—CO—O—, —O—CO—, —CO—CH$_2$—, —CH$_2$—CO—, —CH$_2$O—, —OCH$_2$—, —CH$_2$CH$_2$—, —CH═CH—, —C/C— or a single bond, or
one of the groups Z$^1$ and Z$^2$ is
—(CH$_2$)$_4$—, —(CH$_2$)$_3$CO—, —(CH$_2$)$_2$—O—CO—, —(CH$_2$)$_2$—(CO—O)—, CH═CH—CH$_2$CH$_2$—, —CH$_2$CH2—CH═CH— or —CH$_2$—CH═CH—CH2—, R is H, CN, F, Cl, COOR═, or OH, or alkyl or alkenyl having 1 to 15 or 2 to 15 carbon atoms, respectively, which are unsubstituted, monosubstituted by CN or CF$_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, R═ is H, or alkyl or alkenyl having 1 to 15 or 2 to 15 carbon atoms, respectively, which are unsubstituted, monosubstituted by CN or CF$_3$ or monosubstituted or polysubstituted by halogen, in which one or more CH$_2$ groups are optionally replaced, independently of one another, by —O—, —S—, -◊- —CO—, —CO—O—, —O—CO— or —O—CO—O— in such a way that O atoms are not bonded directly to one another, n is 0, 1 or 2, m is 0 or 1, o is 1, 2 or 3, n+m+o is 2, 3 or 4, $X^1$, $X^2$, $Y^1$, and $Y^2$ are each, independently of one another, including the case where $X^1$, $X^2$, $Y^1$ and/or $Y^2$ occur a number of times, F, Cl, COOR', $NO_2$ or CN, and $p_1$, $p_2$, $q_1$ and $q_2$ are each 0, 1, 2, 3 or 4, and wherein one of the following conditions is fulfilled the compound of formula Ia'has five or more fluorine-substituents in the phenolic moiety, the compound of formula Ia' has one CN group in the phenolic moiety, subject to the proviso that compounds of the formulae A and B are excluded

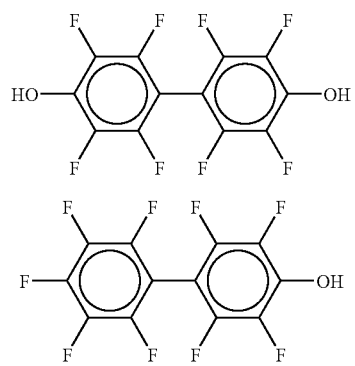

17. A process for preparing a compound of formula Ia'

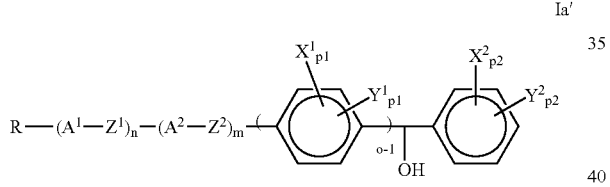

in which $A^1$ and $A^2$ are each, independently of one another, and in the case where $A^1$ occurs a number of times, each $A^1$ is independently of the others:

a) 1,4-cyclohexylene or trans-1,4-cyclohexenylene, in which optionally one or more non-adjacent $CH_2$ groups are replaced by O and/or S, b) 1,4-phenylene, in which optionally one or two CH groups are replaced by N, or c) 1,4-bicyclo[2.2.2]octylene, piperidine-1,4-diyl, naphthalene-2,6-diyl, decahydronaphthalene-3,6-diyl or 1,2,3,4-tetrahydronaphthalene-2,6-diyl, in which (a) and (b) are, independently, unsubstituted, monosubstituted or disubstituted by F atoms, $Z^1$ and $Z^2$ are each, independently of one another, and in the case where $Z^1$ occurs a number of times, each $Z^1$ is independently of the others, —CO—O—, —O—CO—, —CO—$CH_2$—, —$CH_2$—CO—, —$CH_2$O—, —O$CH_2$—, —$CH_2CH_2$—, —CH=CH—, —C/C— or a single bond, or one of the groups $Z^1$ and $Z^2$ is —$(CH_2)_4$—, —$(CH_2)_3$CO—, —$(CH_2)_2$—O—CO—, —$(CH_2)_2$—(CO—O)—, CH=CH—$CH_2CH_2$—, —$CH_2CH_2$—CH=CH— or —$CH_2$—CH=CH—$CH_2$—, R is H, CN, F, Cl, COOR=, or OH, or alkyl or alkenyl having 1 to 15 or 2 to 15 carbon atoms, respectively, which are unsubstituted, monosubstituted by CN or $CF_3$ or monosubstituted or polysubstituted by halogen, in which one or more $CH_2$ groups are optionally replaced, independently of one another, by —O—, —S—, -◊- —CO—, —CO—O—, —O—CO— or —O—CO—O— in such a way that O atoms are not bonded directly to one another, R= is H, or alkyl or alkenyl having 1 to 15 or 2 to 15 carbon atoms, respectively, which are unsubstituted, monosubstituted by CN or $CF_3$ or monosubstituted or polysubstituted by halogen, in which one or more $CH_2$ groups are optionally replaced, independently of one another, by —O—, —S—, -◊- —CO—, —CO—O—, —O—CO— or —O—CO—O— in such a way that O atoms are not bonded directly to one another, n is 0, 1 or 2, m is 0 or 1, o is 1, 2 or 3, n+m+o is 2, 3 or 4, $X^1$, $X^2$, $Y^1$, and $Y^2$ are each, independently of one another, including the case where $X^1$, $X^2$, $Y^1$ and/or $Y^2$ occur a number of times, F, Cl, COOR', $NO_2$ or CN, and $p_1$, $p_2$, $q_1$ and $q_2$ are each 0, 1, 2, 3 or 4, and wherein one of the following conditions is fulfilled the compound of formula Ia' has five or more of $X^1$, $Y^1$, $X^2$, and $Y^2$ as fluorine-substituents, or the compound of formula Ia' has one CN group in the phenolic moiety, subject to the proviso that compounds of the formulae A and B are excluded

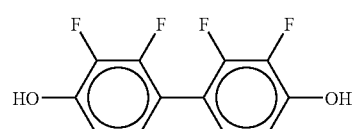

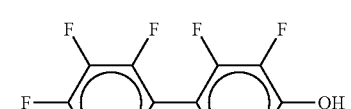

comprising introducing by nucleophilic substitution a phenolic OH group to replace the halogen radical denoted by Hal in the following compound

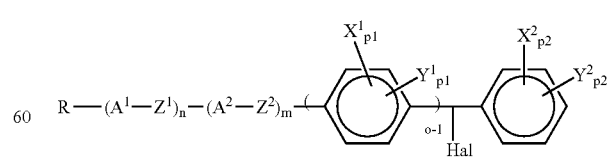

wherein, R, $A^1$, $Z^1$, n, $A^2$, $Z^2$, m, $X^1$, $Y^1$, $X^2$, $Y^2$, $p_1$, $q_1$, $p_2$, $q_2$, and o are defined as in the compound of formula Ia'.

* * * * *

UNITED STATES PATENT AND TRADEMARK OFFICE
CERTIFICATE OF CORRECTION

PATENT NO. : 7,166,337 B2
APPLICATION NO. : 09/907654
DATED : January 23, 2007
INVENTOR(S) : Michael Darius It is certified that error appears in the above-identified patent and that said Letters Patent is hereby corrected as shown below:

Column 44, line 21 reads "Ia-6'" should read -- Ia-6 --
Column 44, line 66 reads $z^1$, should read -- $Z^1$ --
Column 47, line 37 reads $z^1$, should read -- $Z^1$ --
Column 47, first diagram reads " 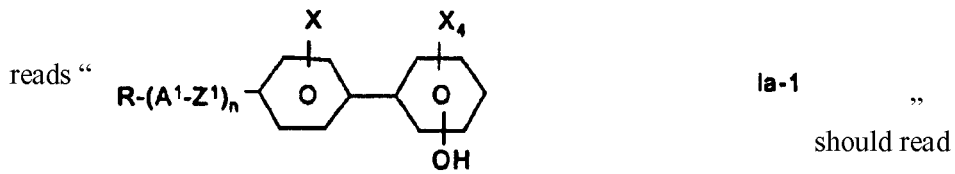 " should read -- 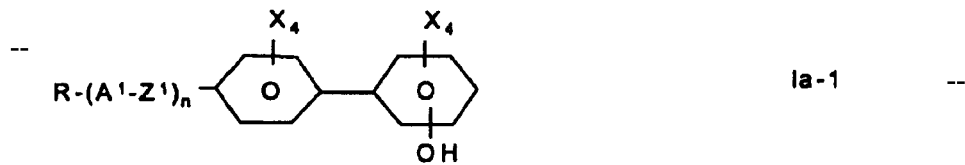 --

Column 48, line 25 reads

" 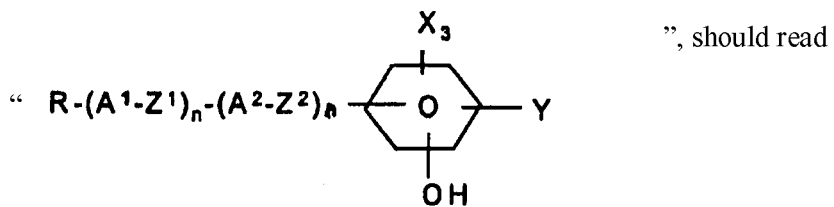 ", should read

-- 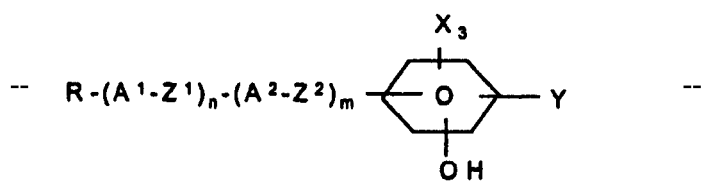 --

UNITED STATES PATENT AND TRADEMARK OFFICE
CERTIFICATE OF CORRECTION

PATENT NO. : 7,166,337 B2
APPLICATION NO. : 09/907654
DATED : January 23, 2007
INVENTOR(S) : Michael Darius It is certified that error appears in the above-identified patent and that said Letters Patent is hereby corrected as shown below:

Column 51 first diagram reads

" 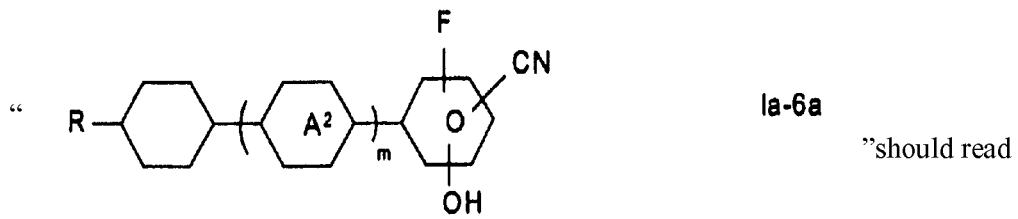 Ia-6a "should read

-- 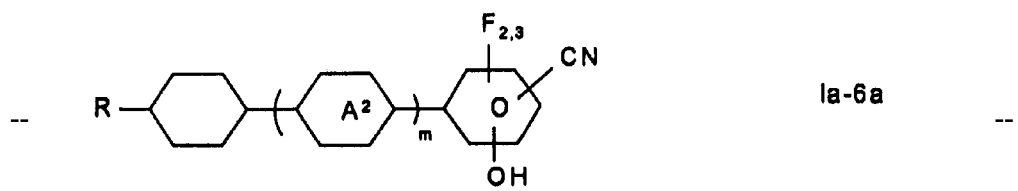 Ia-6a --

Column 52, line 51, reads "wherein

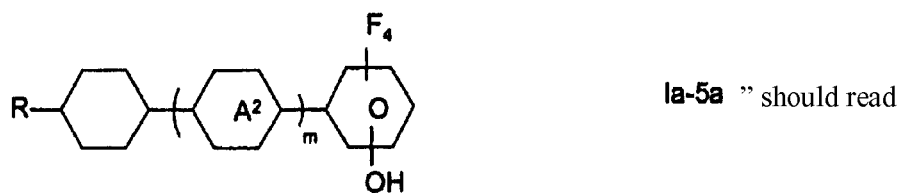 Ia-5a " should read

-- 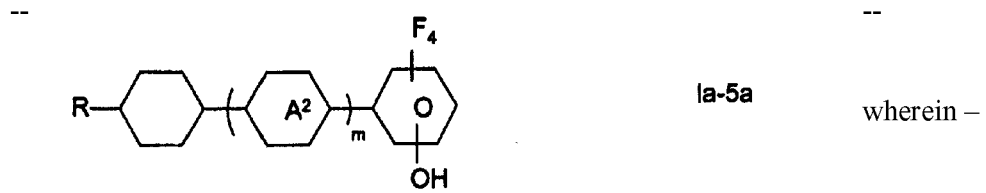 Ia-5a wherein --

Column 53 line 67 reads "$P^2$", should read -- $p^2$ --

UNITED STATES PATENT AND TRADEMARK OFFICE
CERTIFICATE OF CORRECTION

PATENT NO. : 7,166,337 B2
APPLICATION NO. : 09/907654
DATED : January 23, 2007
INVENTOR(S) : Michael Darius It is certified that error appears in the above-identified patent and that said Letters Patent is hereby corrected as shown below:

Column 58 last diagram reads

"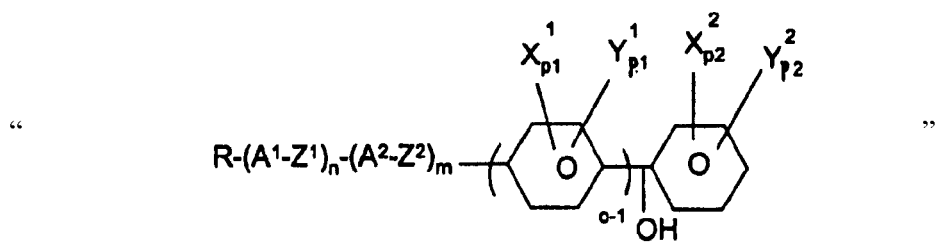"

should read --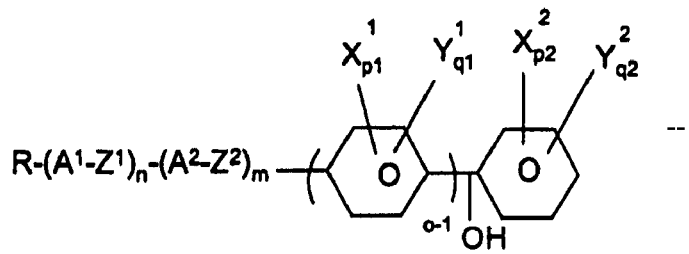--

Signed and Sealed this

Twenty-fifth Day of March, 2008

JON W. DUDAS
*Director of the United States Patent and Trademark Office*